(12) United States Patent
Robinson et al.

(10) Patent No.: US 12,178,725 B1
(45) Date of Patent: Dec. 31, 2024

(54) SELF-ADJUSTING SOCKET FOR LOWER LIMB PROSTHESIS

(71) Applicant: VESSL PROSTHETICS INC., Ilderton (CA)

(72) Inventors: Sydney Motz Robinson, London (CA); Oleksiy Zaika, Ilderton (CA); Sajed Cela, London (CA)

(73) Assignee: Vessl Prosthetics Inc., Ilderton (CA)

( * ) Notice: Subject to any disclaimer, the term of this patent is extended or adjusted under 35 U.S.C. 154(b) by 0 days.

(21) Appl. No.: 18/413,606

(22) Filed: Jan. 16, 2024

(51) Int. Cl.
*A61F 2/80* (2006.01)
*A61F 2/50* (2006.01)
*A61F 2/68* (2006.01)

(52) U.S. Cl.
CPC ............... *A61F 2/80* (2013.01); *A61F 2/68* (2013.01); *A61F 2002/5036* (2013.01); *A61F 2002/5072* (2013.01)

(58) Field of Classification Search
CPC ...... A61F 2/60; A61F 2/70; A61F 2/80; A61F 2002/5016; A61F 2002/5023; A61F 2002/5027; A61F 2002/5036; A61F 2002/5072
See application file for complete search history.

(56) References Cited

U.S. PATENT DOCUMENTS

| | | | |
|---|---|---|---|
| 2,229,728 A | 1/1941 | Whitfield | |
| 3,889,301 A | 6/1975 | Bonner, Sr. | |
| 4,923,475 A | 5/1990 | Gosthnian et al. | |
| 5,133,776 A | 7/1992 | Crowder | |
| 5,156,629 A | 10/1992 | Shane et al. | |
| 6,155,120 A | 12/2000 | Taylor | |
| 6,543,299 B2 | 4/2003 | Taylor | |
| 6,585,774 B2 | 7/2003 | Dean, Jr. et al. | |
| 6,666,894 B2 | 12/2003 | Perkins et al. | |
| 6,936,073 B2 | 8/2005 | Karason | |
| 6,991,657 B1 | 1/2006 | Price, Jr. | |
| 7,201,063 B2 | 4/2007 | Taylor | |
| 7,468,079 B2 | 12/2008 | Collier | |

(Continued)

FOREIGN PATENT DOCUMENTS

| CA | 2686173 C | 10/2015 |
|---|---|---|
| CA | 2845518 C | 7/2020 |

(Continued)

OTHER PUBLICATIONS

Hao Zheng et al., "Design and Control of a Pneumatically Actuated Transtibial Prosthesis", Science Direct, Journal of Bionic Engineering, vol. 12, No. 2, 2015, pp. 217-226.

*Primary Examiner* — Christie Bahena
(74) *Attorney, Agent, or Firm* — TUCKER ELLIS LLP

(57) ABSTRACT

The present disclosure describes self-adjusting sockets for lower limb prostheses in which each step transmits motion to a resilient resistive element coupled to a reciprocal actuator. The resistive element can transmit the motion to the reciprocal actuator to cycle the reciprocal actuator. Each cycle of the reciprocal actuator acts through a mechanical linkage to tighten the socket around the residuum, until a desired threshold tightness on the residuum is reached. After the threshold tightness is reached, the resistive element yields and absorbs the motion rather than transmitting the motion, so that the reciprocal actuator ceases to cycle on each step, preventing further tightening beyond the threshold.

18 Claims, 23 Drawing Sheets

(56) References Cited

U.S. PATENT DOCUMENTS

| | | |
|---|---|---|
| 7,655,049 B2 | 2/2010 | Phillips |
| 7,670,386 B2 | 3/2010 | Ezenwa |
| 8,282,686 B2 | 10/2012 | McKinney |
| 8,303,670 B2 | 11/2012 | Martin et al. |
| 8,443,501 B2 * | 5/2013 | Mahon ............ A61F 2/80 29/244 |
| 8,491,667 B2 | 7/2013 | Dillingham |
| 8,568,489 B2 | 10/2013 | Finlinson et al. |
| 8,795,385 B2 | 8/2014 | Bache |
| 8,845,755 B2 | 9/2014 | Dillingham |
| 8,951,211 B2 | 2/2015 | Sanders et al. |
| 9,241,812 B2 | 1/2016 | Martin et al. |
| 9,254,200 B2 | 2/2016 | Galea et al. |
| 9,345,590 B2 | 5/2016 | Arabian et al. |
| 9,468,543 B2 | 10/2016 | Hurley et al. |
| 9,504,585 B2 | 11/2016 | Cornell |
| 9,554,923 B2 | 1/2017 | Kettwig et al. |
| 9,956,094 B2 | 5/2018 | Mahon |
| 9,980,779 B2 | 5/2018 | Hurley et al. |
| 10,004,614 B1 | 6/2018 | Johnson |
| 10,161,838 B2 | 12/2018 | Huang et al. |
| 10,278,837 B1 | 5/2019 | Martin |
| 10,357,382 B2 | 7/2019 | Ballas et al. |
| 10,406,003 B2 | 9/2019 | Johnson |
| 10,806,608 B2 | 10/2020 | Dillingham |
| 10,864,093 B2 | 12/2020 | Hajiaghaei |
| 10,918,502 B2 | 2/2021 | Mahon |
| 10,918,503 B2 | 2/2021 | Bache et al. |
| 11,058,562 B2 | 7/2021 | Pawlik et al. |
| 11,083,602 B2 | 8/2021 | Mahon |
| 11,141,294 B2 | 10/2021 | Halldorsson et al. |
| 11,173,057 B2 | 11/2021 | Smith et al. |
| 11,246,723 B2 | 2/2022 | Harris et al. |
| 11,246,724 B2 | 2/2022 | Bache et al. |
| 11,504,252 B2 | 11/2022 | Mahon |
| 11,596,531 B2 | 3/2023 | Pawlik et al. |
| 11,617,667 B2 | 4/2023 | Will et al. |
| 11,684,496 B2 | 6/2023 | Phillips |
| 11,759,338 B2 | 9/2023 | Mahon |
| 11,806,253 B2 | 11/2023 | Mahon et al. |
| 11,844,667 B2 * | 12/2023 | Johnson ............ A61F 2/80 |
| 2003/0078674 A1 | 4/2003 | Phillips |
| 2007/0055384 A1 | 3/2007 | Perkins et al. |
| 2011/0060421 A1 | 3/2011 | Martin et al. |
| 2013/0218296 A1 | 8/2013 | Koniuk et al. |
| 2013/0274895 A1 | 10/2013 | Pacanowsky et al. |
| 2014/0331412 A1 | 11/2014 | Taylor |
| 2015/0018974 A1 | 1/2015 | Dillingham |
| 2015/0313730 A1 | 11/2015 | Hurley et al. |
| 2016/0045340 A1 | 2/2016 | Vaughan et al. |
| 2016/0158035 A1 | 6/2016 | Alley |
| 2016/0278949 A1 | 9/2016 | Dillingham |
| 2016/0331562 A1 * | 11/2016 | Bache ............ A61F 2/80 |
| 2017/0027720 A1 | 2/2017 | Pedtke et al. |
| 2017/0095356 A1 | 4/2017 | Hurley et al. |
| 2017/0156896 A1 | 6/2017 | Alley |
| 2018/0020973 A1 | 1/2018 | Hurley et al. |
| 2019/0298547 A1 | 10/2019 | Wood |
| 2019/0388250 A1 | 12/2019 | Johnson |
| 2020/0022819 A1 | 1/2020 | Hurley et al. |
| 2020/0022826 A1 | 1/2020 | Bache |
| 2020/0113715 A1 | 4/2020 | Bache et al. |
| 2020/0297514 A1 | 9/2020 | Prescott et al. |
| 2020/0345520 A1 | 11/2020 | Sanders et al. |
| 2020/0352748 A1 | 11/2020 | Dillingham |
| 2021/0015635 A1 | 1/2021 | Martin |
| 2021/0038455 A1 | 2/2021 | Kokko et al. |
| 2021/0113356 A1 | 4/2021 | Laszczak et al. |
| 2021/0298927 A1 | 9/2021 | Phillips |
| 2021/0361447 A1 | 11/2021 | Mahon |
| 2021/0378844 A1 | 12/2021 | Harding et al. |
| 2022/0062014 A1 | 3/2022 | Martin |
| 2022/0110768 A1 | 4/2022 | Ballas et al. |
| 2022/0287858 A1 | 9/2022 | Accinni |
| 2022/0304833 A1 | 9/2022 | Sandahl et al. |
| 2023/0034391 A1 | 2/2023 | Martin |
| 2023/0201011 A1 | 6/2023 | Granz et al. |
| 2023/0270573 A1 | 8/2023 | Jonasson et al. |
| 2023/0277341 A1 | 9/2023 | Sanders et al. |
| 2023/0346576 A1 | 11/2023 | Will et al. |
| 2024/0065870 A1 | 2/2024 | Miller et al. |

FOREIGN PATENT DOCUMENTS

| | | |
|---|---|---|
| CN | 219250566 U | 6/2023 |
| CN | 220046202 U | 11/2023 |
| DE | 896543 C | 11/1953 |
| DE | 314985 C | 10/2019 |
| DE | 102021133616 A1 | 6/2023 |
| EP | 1549263 B1 | 6/2010 |
| EP | 2775967 B1 | 1/2019 |
| EP | 3639794 A1 | 4/2020 |
| EP | 3725271 A1 | 10/2020 |
| EP | 3527175 B1 | 12/2021 |
| EP | 3355838 B1 | 5/2022 |
| EP | 4312896 A1 | 2/2024 |
| GB | 2435216 A | 8/2007 |
| GB | 2566307 B | 4/2022 |
| JP | 6969720 B2 | 11/2021 |
| KR | 102364372 B1 | 2/2022 |
| KR | 102434955 B1 | 8/2022 |
| MX | 357076 B | 6/2018 |
| TW | 202222279 A | 6/2022 |
| WO | 1995003760 A1 | 2/1995 |
| WO | 2003009787 A2 | 2/2003 |
| WO | 2013071308 A1 | 5/2013 |
| WO | 2017096069 A1 | 6/2017 |
| WO | 2017221019 A1 | 12/2017 |
| WO | 2019180431 A1 | 9/2019 |
| WO | 2020257233 A1 | 12/2020 |
| WO | 2021032228 A1 | 2/2021 |
| WO | 2022207635 A1 | 10/2022 |
| WO | 2023031191 A1 | 3/2023 |
| WO | 2023172831 A1 | 9/2023 |

* cited by examiner

SELF-ADJUSTING SOCKET FOR LOWER LIMB PROSTHESIS

TECHNICAL FIELD

The present disclosure relates to sockets for lower limb prostheses, and more particularly to self-adjusting sockets for lower limb prostheses.

BACKGROUND

Amputation of a limb is tragic. Fortunately, medical technology has advanced considerably, and a wide range of prosthetic limbs are now available.

A prosthetic limb typically consists of a prosthetic socket, an alignment device, one or more pylons, and an end effector. The prosthetic socket interfaces with the residual limb, or residuum, and connects it to the rest of the prosthetic limb. The alignment device typically maintains proper alignment between the socket and the rest of the prosthesis. The pylon(s) connect the socket and/or alignment device to the end effector. There may be a single pylon (e.g. for transtibial and transradial amputees) or multiple pylons (e.g. for transfemoral and transhumeral amputees) pylon(s) that connect the socket and/or alignment device to the end effector. The end effector typically replicates a foot or hand, depending on whether the prosthesis is for an upper limb (transhumeral, transradial) or lower limb (transfemoral, transtibial) amputee. In the case of a transfemoral amputee, the prosthetic limb also typically includes a knee joint.

Arguably the most important component of a prosthetic limb is the prosthetic socket. It is the sole component connecting the residuum to the rest of the prosthetic limb. Effective interface (fit) between the socket and the residuum is crucial.

A major complication in achieving an effective interface between the socket and the residuum is the fact that the size and shape of the residuum is not constant, but fluctuates over time. These fluctuations include short term fluctuations and long term fluctuations.

Following amputation, the edema, or swelling, decreases and muscles in the residuum may atrophy from disuse, which leads to significant changes in the residuum's volume.

These are examples of relatively long term fluctuations, which may be accommodated straightforwardly, for example by the expedient of taking periodic measurements. In the acute phase following amputation (approximately two years post-amputation), an amputee typically requires several "check sockets" which are simple sockets that are used to check whether the fit is appropriate. Since the residuum loses significant volume from edema and muscle atrophy, amputees require a series of check sockets until their residuum volume has become sufficiently stable and does not decrease as significantly week-to-week.

Unfortunately, change in the volume of the residuum is not only an acute issue following amputation, but often persists throughout an amputee's life. Moreover, short term changes in volume are common, and the volume of the residuum can change considerably over the course of a single day or even a few hours. Factors that can affect the volume of the residuum include, but are not limited to, exercise, diet, lifestyle, and other comorbidities, as well as weather.

Since conventional prosthetic sockets are rigid and unchanging in size and shape, a change in the residuum's volume alters the socket fit, that is, the interface between the socket and residuum. Typically, an amputee will progressively lose volume over the long term, as a result of edema reduction and muscle loss, and the volume will oscillate over the short term. Activities of daily living, which include any kind of ambulation, can drive fluid out of the limb, reducing its volume.

Prosthetic socks may be used to accommodate the longer term decreases in volume-more socks and/or thicker socks may be used as residuum volume decreases over time. However, prosthetic socks are not well suited to accommodate the shorter term fluctuations in residuum volume, as they would require the amputee to remove their prosthetic limb, add socks on top of their residuum, and then reattach the prosthetic limb. Adding or removing prosthetic socks is extremely disruptive to an amputee's activities of daily living; they must sit down to remove their prosthetic limb and rearrange or remove articles of clothing to access their residuum and add or remove prosthetic socks appropriately. They must also bring socks with them to every destination in case the need to add or remove prosthetic socks arises. Typically, amputees must add several prosthetic socks (in some cases, over 10) to properly account for the volume they lost in their residuum.

Furthermore, even if adding or removing socks throughout the day were practical, prosthetic socks can only compensate for a finite amount of volume change, and do not accommodate changes in the shape of the residuum that may result from the volume changes. As a result, painful forces can act on a part or parts of the residuum (particularly those areas with bony protrusions).

It has been observed that daily fluctuations in residuum volume for a femoral residuum or a tibial residuum typically occur at the posterior of the residuum. One attempt to address the daily fluctuations in residuum volume is described in U.S. Pat. No. 7,655,049 to Phillips, which describes a prosthetic device having a socket with an insert having a bladder system for monitoring and compensating for volume fluctuations in a residual limb. A plurality of bladders are preferably provided, in one embodiment, substantially only on a posterior portion of the socket. The bladders may be organized into zones, with the zones being inflatable to differing pressures depending on volume fluctuations in a residual limb. Pressure sensors may be provided for each bladder or for each zone, and flow regulators may be provided to control fluid flow into or out of the bladders or zones of bladders based on readings from the pressure sensors to control volume within the insert. Alternatively, bladders can be manually inflated depending on an amputee's needs.

As can be imagined, this system requires complex sensors and electronic arrangements, which result in increased complexity and cost, or manual adjustment, which increases the inconvenience for the amputee.

SUMMARY

Broadly speaking, present disclosure describes self-adjusting sockets for lower limb prostheses in which each step transmits motion to a resilient resistive element coupled to a reciprocal actuator. The resistive element can transmit the motion to the reciprocal actuator to cycle the reciprocal actuator. Each cycle of the reciprocal actuator acts through a mechanical linkage to tighten the socket around the residuum, until a threshold tightness on the residuum is reached. After the threshold tightness is reached, the resistive element yields and absorbs the motion rather than transmitting the motion, so that the reciprocal actuator ceases to cycle on each step, preventing further tightening beyond the threshold.

In one aspect, a self-adjusting socket for a lower limb prosthesis comprises a housing, a retention mechanism, at least one reciprocal actuator, and a locking mechanism. The housing comprises a residuum receptacle, and a retention mechanism is carried by the housing and configured for retaining a residuum within the residuum receptacle. The reciprocal actuator(s) are carried by the housing and coupled to the retention mechanism through a respective mechanical linkage, and configured to act through the respective mechanical linkage to incrementally tighten the retention mechanism against the residuum on each cycle of the reciprocal actuator(s). The locking mechanism is carried by the housing and configured to maintain tightness of the retention mechanism against the residuum after each cycle of the reciprocal actuator(s). The housing is configured so that each step transmits motion to a respective resilient resistive element coupled to a respective reciprocal actuator. When the tightness of the retention mechanism is below a threshold, each step transmits motion across the respective resistive element to the respective reciprocal actuator to cycle the respective reciprocal actuator. When the tightness of the retention mechanism has reached the threshold, on each further step the respective resistive element yields to absorb the motion, so that the respective reciprocal actuator fails to cycle on each further step, inhibiting further tightening of the retention mechanism beyond the threshold.

In a preferred embodiment, the locking mechanism is a releasable locking mechanism.

A preferred embodiment of the socket further comprises a manual tightening mechanism for tightening the retention mechanism.

In an embodiment, the retention mechanism comprises at least one panel movably carried by the housing, with the panel(s) being movable inwardly and outwardly relative to the residuum receptacle and the reciprocal actuator(s) is configured to act through the respective mechanical linkage to incrementally move the panel(s) inwardly to tighten the panel(s) against the residuum on each cycle of the reciprocal actuator(s). In a particular embodiment, the panel(s) are a plurality of panels that are arranged circumferentially about the residuum receptacle. In a more particular embodiment, the panels are disposed in respective openings so as to be inwardly and outwardly displaceable relative to the housing. In a yet more particular embodiment, the mechanical linkage comprises at least one cable coupled to the panels, and each respective reciprocal actuator is configured to incrementally increase tension in the respective cable on each cycle of the respective reciprocal actuator, whereby incrementally increasing the tension on the respective cable moves the respective panels inwardly relative to the residuum receptacle.

In an embodiment, the housing carries a movable platform. The platform is reciprocally movable toward and away from the residuum receptacle between a distal position and a proximal position, and the platform is biased into the distal position. Each of the reciprocal actuator(s) is carried by the housing between the residuum receptacle and the platform. The respective resistive element is trapped between the platform and the respective reciprocal actuator whereby movement of the platform toward the proximal position pushes the resistive element toward the respective reciprocal actuator. Reciprocal movement of the platform into the proximal position and back to the distal position cycles the respective reciprocal actuator only where a resistance to compression of the respective resistive element exceeds a resistance to movement from the tension in the respective cable so that the respective resistive element transmits the movement of the platform to the respective reciprocal actuator instead of yielding to the movement of the platform.

In some embodiments, each reciprocal actuator comprises a rocker coupled to a respective spool, and each cycle of the rocker indexes the spool to wind the respective cable onto the spool to incrementally increase the tension in the respective cable. In particular embodiments, each rocker may comprises a respective outwardly extending actuator arm that acts as a lever to pivot the rocker, and, where the resistance to compression of the respective resistive element exceeds a resistance to movement from the tension in the respective cable, the resistive element transmits the movement of the platform into the proximal position to the actuator arm to pivot the rocker and thereby index the spool.

In some embodiments, the resistive element(s) may be at least one spring.

In another aspect, a method for securing a residuum in a socket of a lower limb prosthesis is provided. Motion from steps taken with the lower limb prosthesis is transmitted across a resilient resistive element to a reciprocal actuator to cycle the reciprocal actuator, where each cycle of the reciprocal actuator incrementally tightens a retention mechanism against the residuum until a tightness threshold of the retention mechanism is reached. After the tightness threshold is reached, motion from further steps taken with the lower limb prosthesis is transmitted into the resistive element wherein the resistive element yields and absorbs the motion so that the reciprocal actuator fails to cycle on each further step, inhibiting further tightening of the retention mechanism beyond the threshold.

In some embodiments of the method, each cycle of the reciprocal actuator incrementally winds a cable around a spool to increase tension in the cable, and the cable is coupled to the retention mechanism and increasing the tension in the cable tightens the retention mechanism. In particular embodiments, increasing the tension in the cable tightens the retention mechanism by forcing a panel inwardly against the residuum.

In some embodiments, the resistive element is a spring.

In a still further aspect, a method for tightening a panel in a receptacle for a residuum is provided. The method comprises applying incremental tension across the panel to move the panel inwardly relative to the receptacle. The incremental tension is applied by transmission of movement of an end effector of a lower limb prosthesis toward the residuum through a mechanical interface to a tensioner, and the movement is transmitted to the tensioner only when a resistance of the mechanical interface exceeds a current tension applied by the tensioner.

In some embodiments, the resistance of the mechanical interface may be provided by at least one spring.

In some embodiments, the tensioner may comprise a winch.

BRIEF DESCRIPTION OF THE DRAWINGS

These and other features will become more apparent from the following description in which reference is made to the appended drawings wherein:

FIG. 13AE is an enlargement of FIG. 13A to show detail;

FIG. 13BE is an enlargement of FIG. 13B to show detail;

FIG. 13CE is an enlargement of FIG. 13C to show detail;

DETAILED DESCRIPTION

Figure 1:
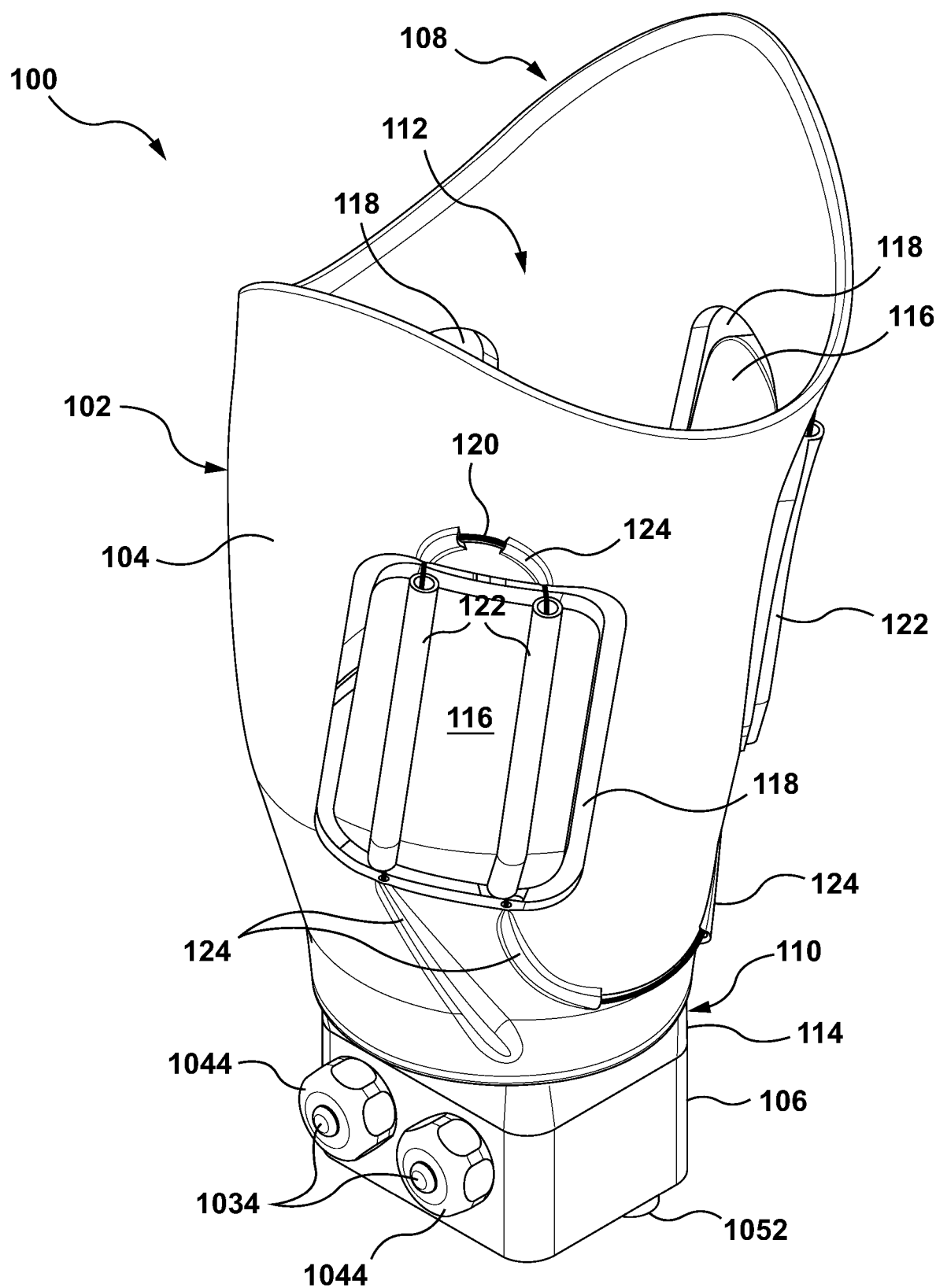
FIG. 1 is a top perspective view of an illustrative embodiment of a self-adjusting socket for a lower limb prosthesis, according to an aspect of the present disclosure.
Figure 2:
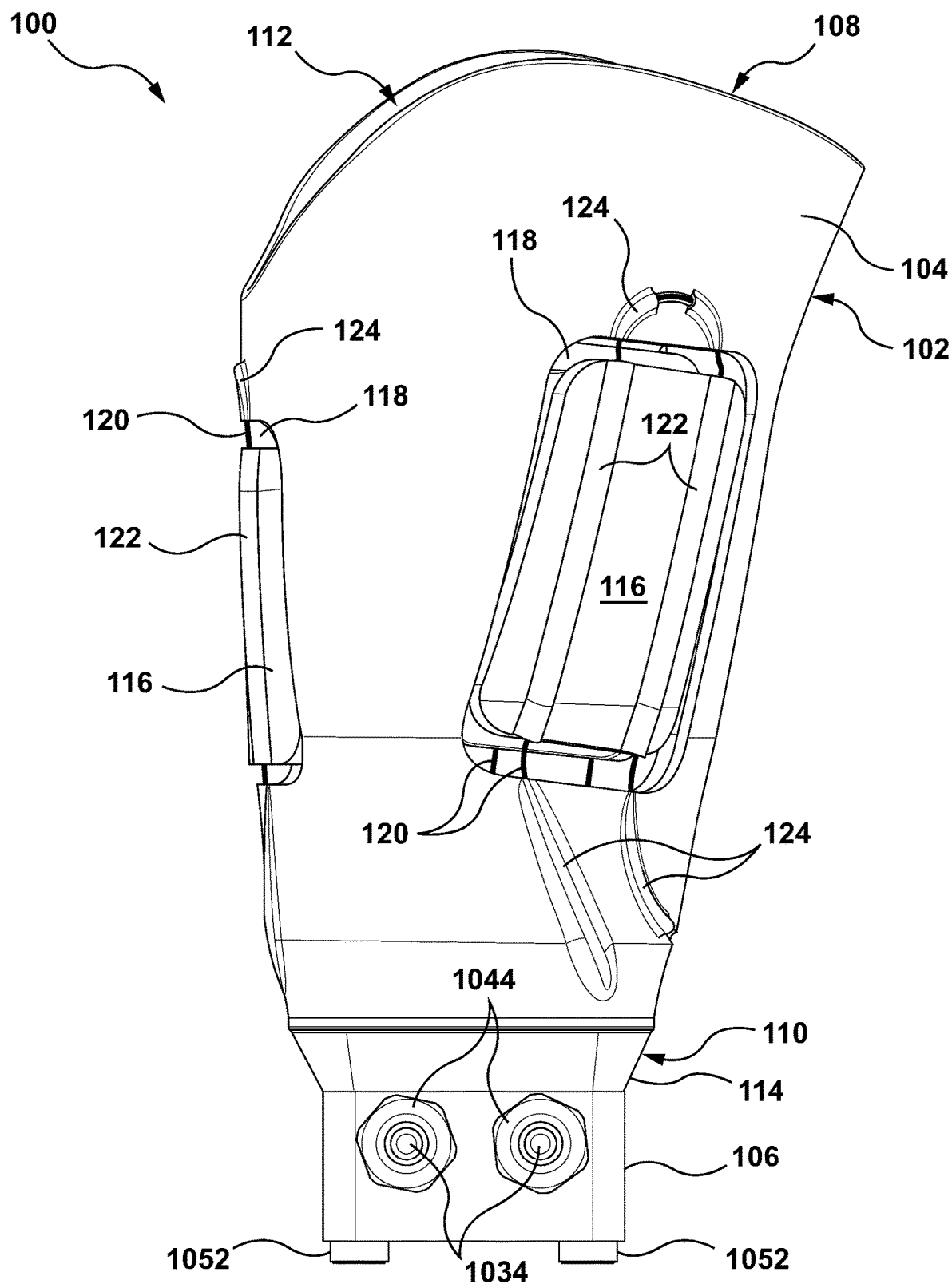
FIG. 2 is a first side elevation view of the self-adjusting socket of FIG. 1.
Figure 3:
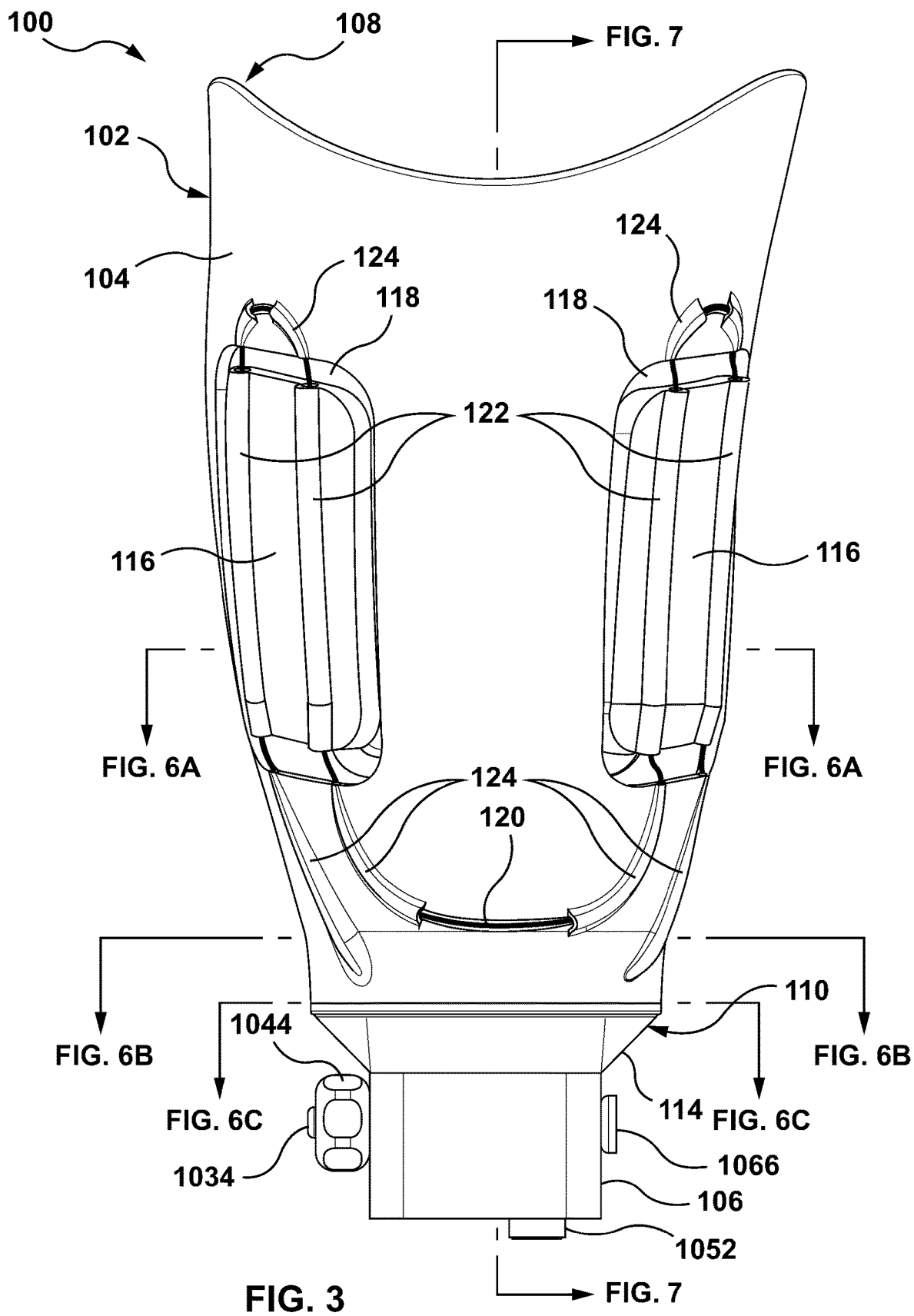
FIG. 3 is a front elevation view of the self-adjusting socket of FIG. 1.
Figure 4:
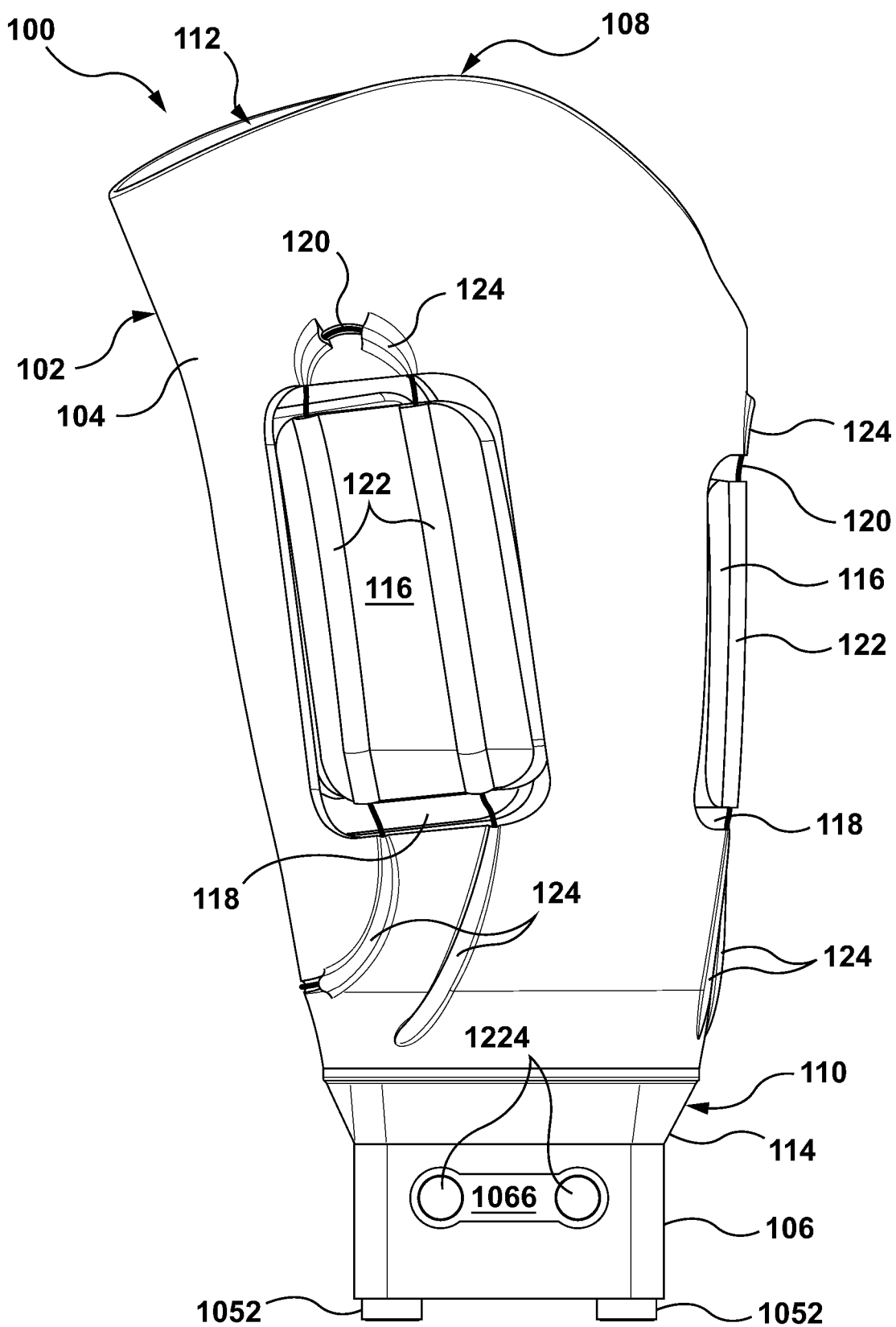
FIG. 4 is a second side elevation view of the self-adjusting socket of FIG. 1.
Figure 5:
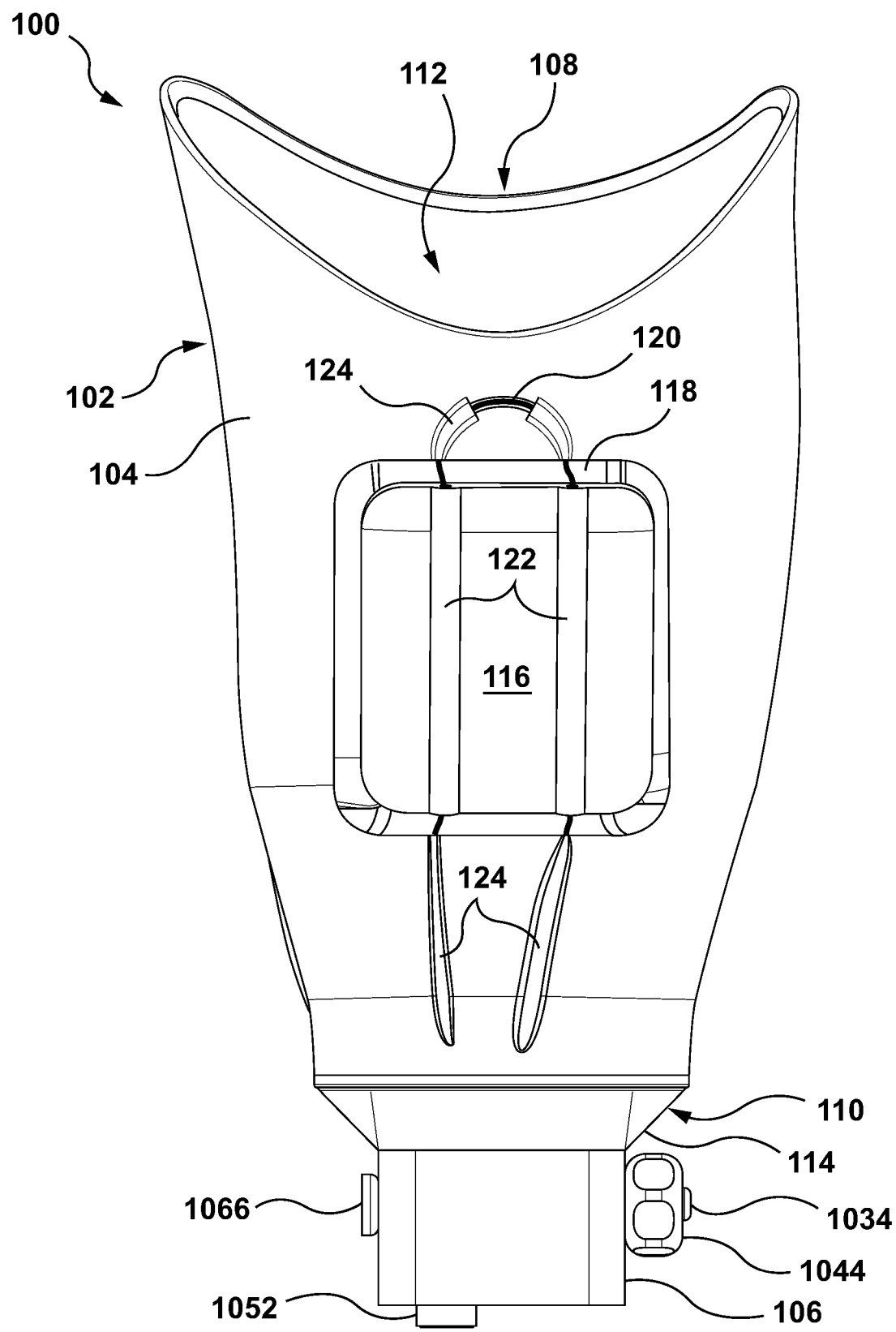
FIG. 5 is a rear side elevation view of the self-adjusting socket of FIG. 1.
Figure 6:
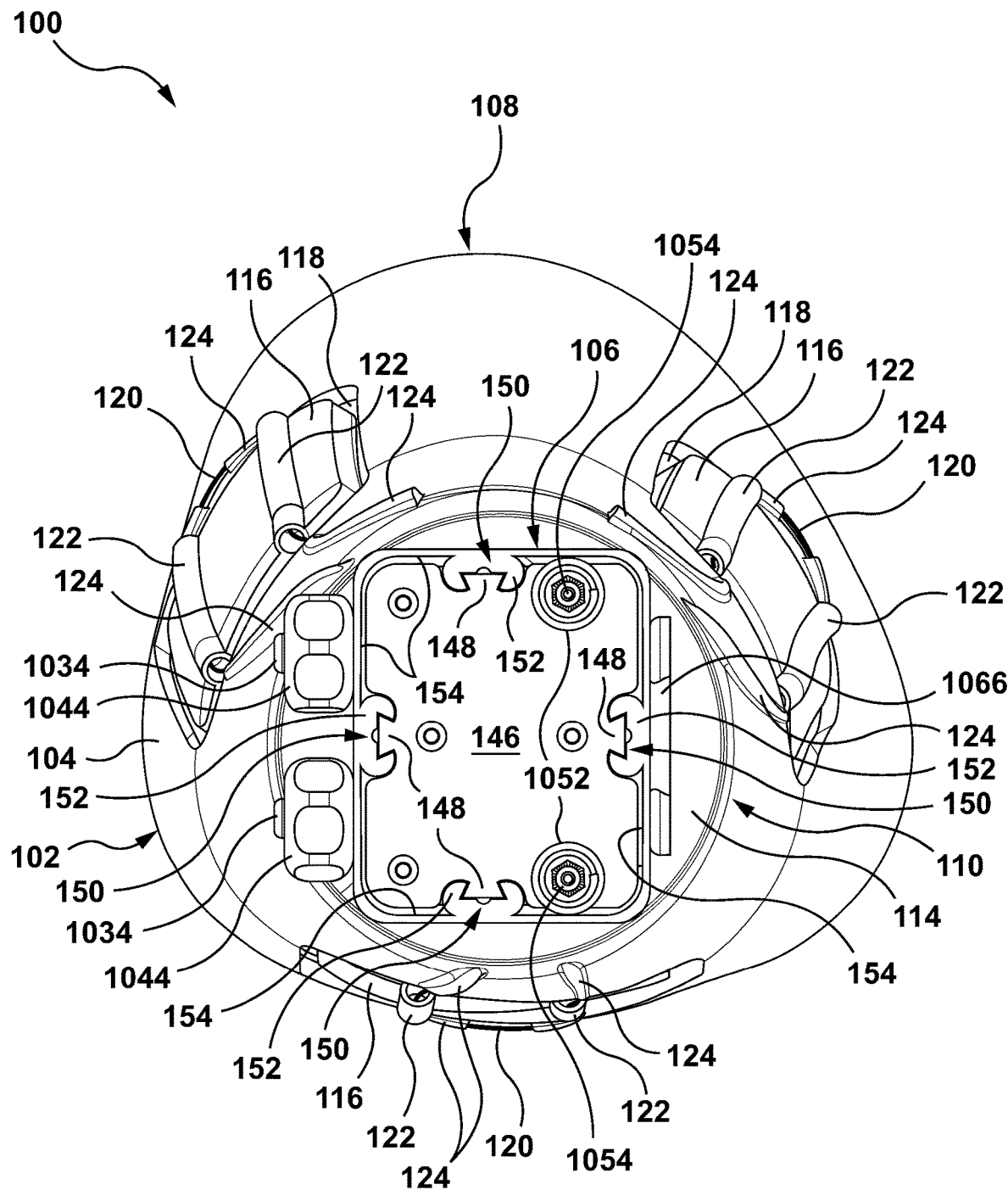
FIG. 6 is a bottom plan view of the self-adjusting socket of FIG. 1.
Figure 6A:
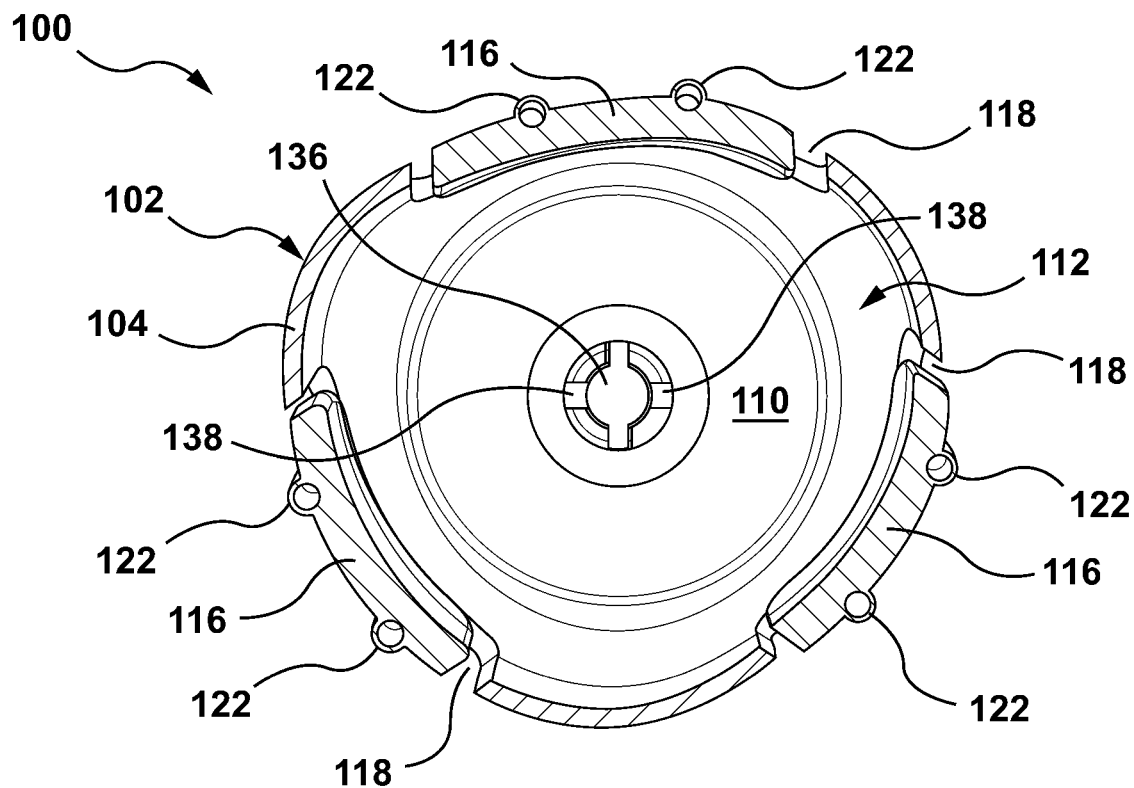
FIG. 6A is a cross-sectional view taken along the line 6A-6A in FIG. 3.
Figure 6B:
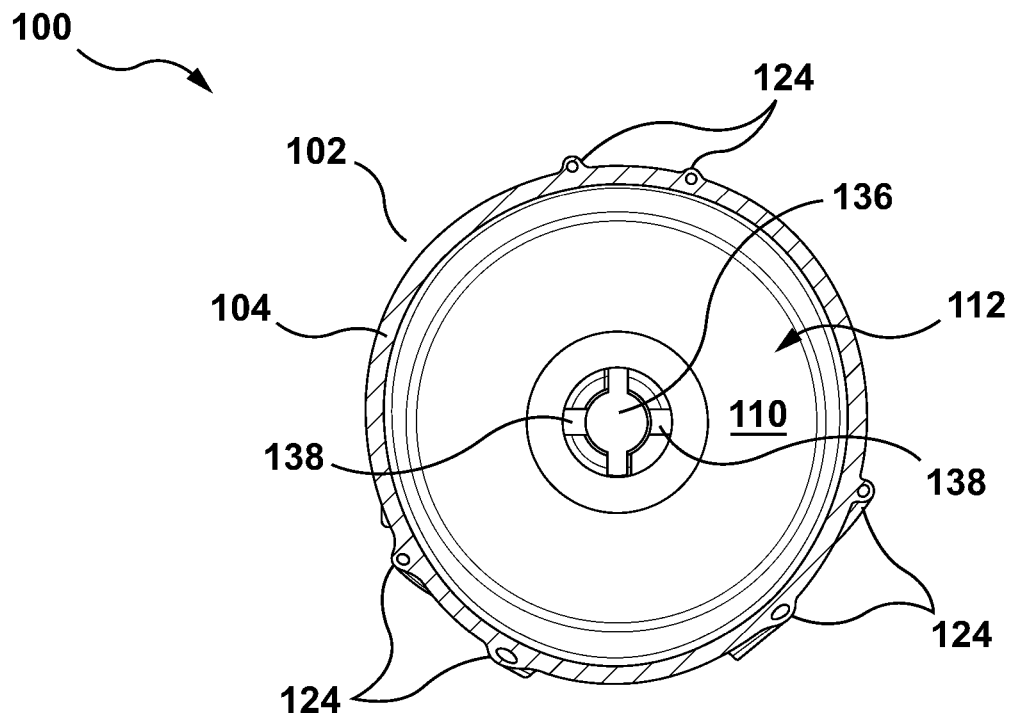
FIG. 6B is a cross-sectional view taken along the line 6B-6B in FIG. 3.
Figure 6C:
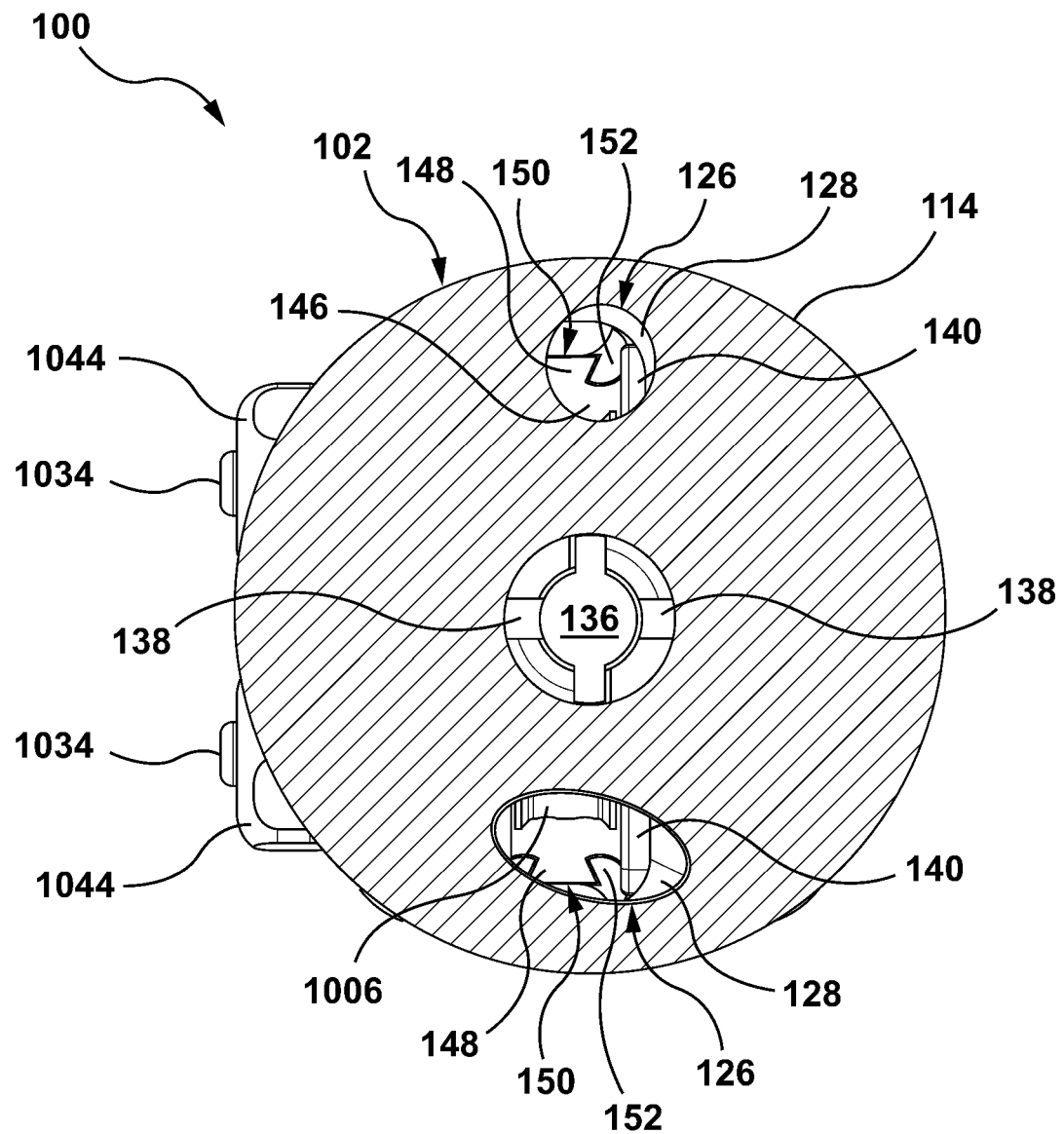
FIG. 6C is a cross-sectional view taken along the line 6C-6C in FIG. 3.

Reference is now made to FIGS. 1 to 6, which show a non-limiting illustrative embodiment of a self-adjusting socket 100 for a lower limb prosthesis. The illustrative socket 100 is for a transtibial prosthesis, but one of ordinary skill in the art, now informed by the present disclosure, can adapt the present disclosure for use with a socket for a transfemoral amputee. Thus, sockets as described herein may be incorporated into a complete prosthetic for a transtibial or transfemoral amputee. The self-adjusting socket 100 comprises a housing 102, which in turn comprises a receptacle body 104 and an actuator enclosure 106 carried by the receptacle body 104. The receptacle body 104 is generally hollow with an open end 108 and a support end 110 opposite the open end 108, and the interior volume of the receptacle body 104 forms a residuum receptacle 112 adapted to receive the residuum of an amputee via the open end 108. Thus, the housing 102, in particular the receptacle body 104 thereof, comprises a residuum receptacle 112.

In the illustrated embodiment, a mounting block 114 is disposed at the support end 110 of the receptacle body 104 and the actuator enclosure 106 is releasably mounted to the mounting block 114. In the illustrated embodiment, the mounting block 114 is formed monolithically with the receptacle body 104, in other embodiments the mounting block may be a separate part. In still other embodiments, the actuator enclosure may be mounted directly to the support end of the receptacle body, or may be monolithically formed therewith.

The housing 102 carries a retention mechanism configured for retaining a residuum within the residuum receptacle 112. In the illustrated embodiment, the retention mechanism comprises three panels 116 movably carried by the housing 102, in particular the receptacle body 104 thereof, so that the panels 116 are movable inwardly and outwardly relative to the residuum receptacle 112. As shown, the panels 116 are arranged circumferentially about the residuum receptacle 112, and are disposed in respective openings 118 in the receptacle body 104 so as to be inwardly and outwardly displaceable relative to the receptacle body 104 of the housing 102. In other embodiments, more or fewer panels may be present, or an alternate retention mechanism may be used. The panels may include interiorly facing pads for cushioning. The panels 116 shown for the illustrative socket 100 are configured for a transtibial amputee; an alternate configuration, as will be apparent to one of ordinary skill in the art, now informed by the present disclosure, may be adapted for a transfemoral amputee.

Figure 7A:
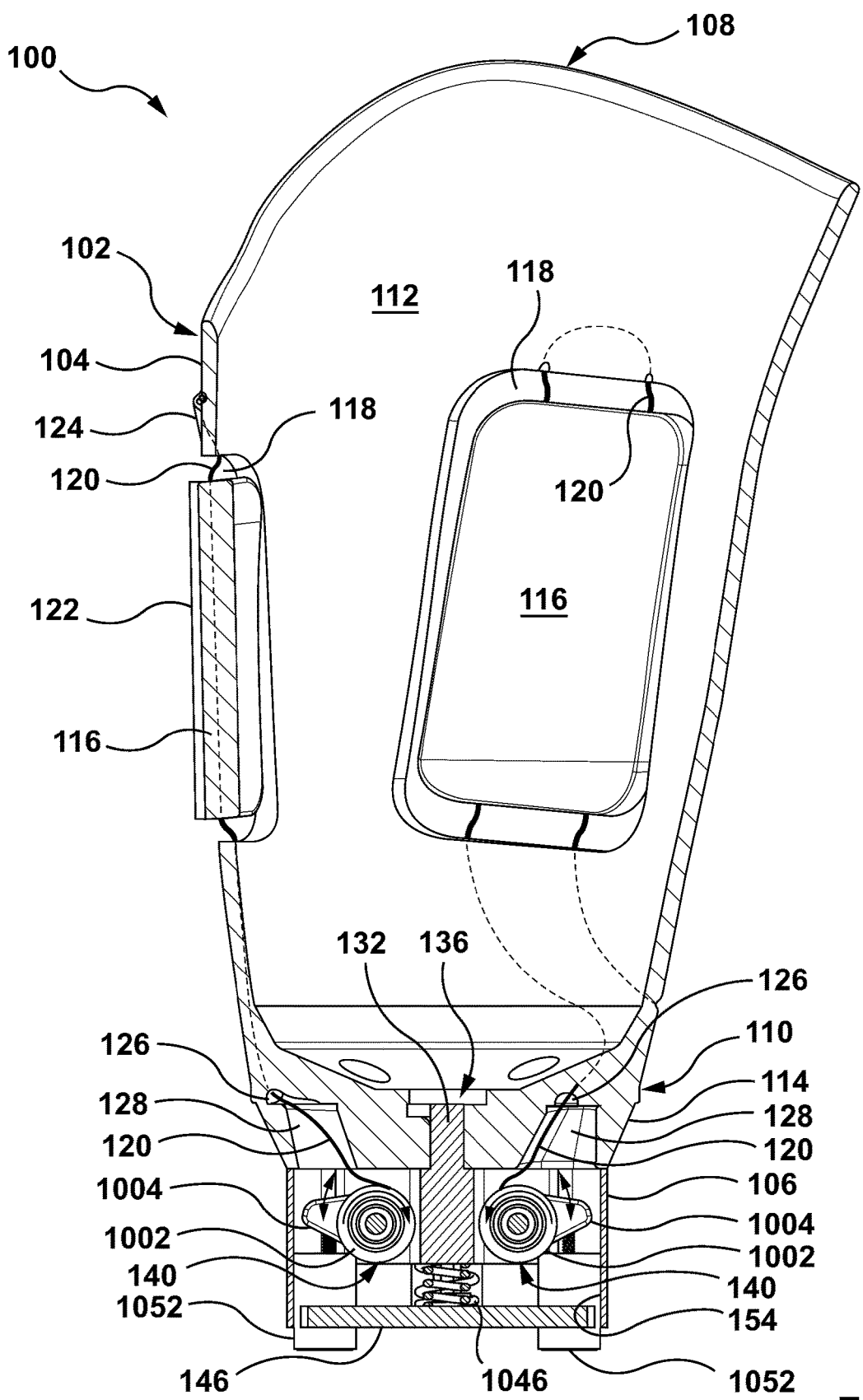
FIG. 7A is a cross-sectional view taken along the line 7-7 in FIG. 3, showing a first position of the panels of the self-adjusting socket of FIG. 1, when there is slack in the cables thereof.
Figure 7B:
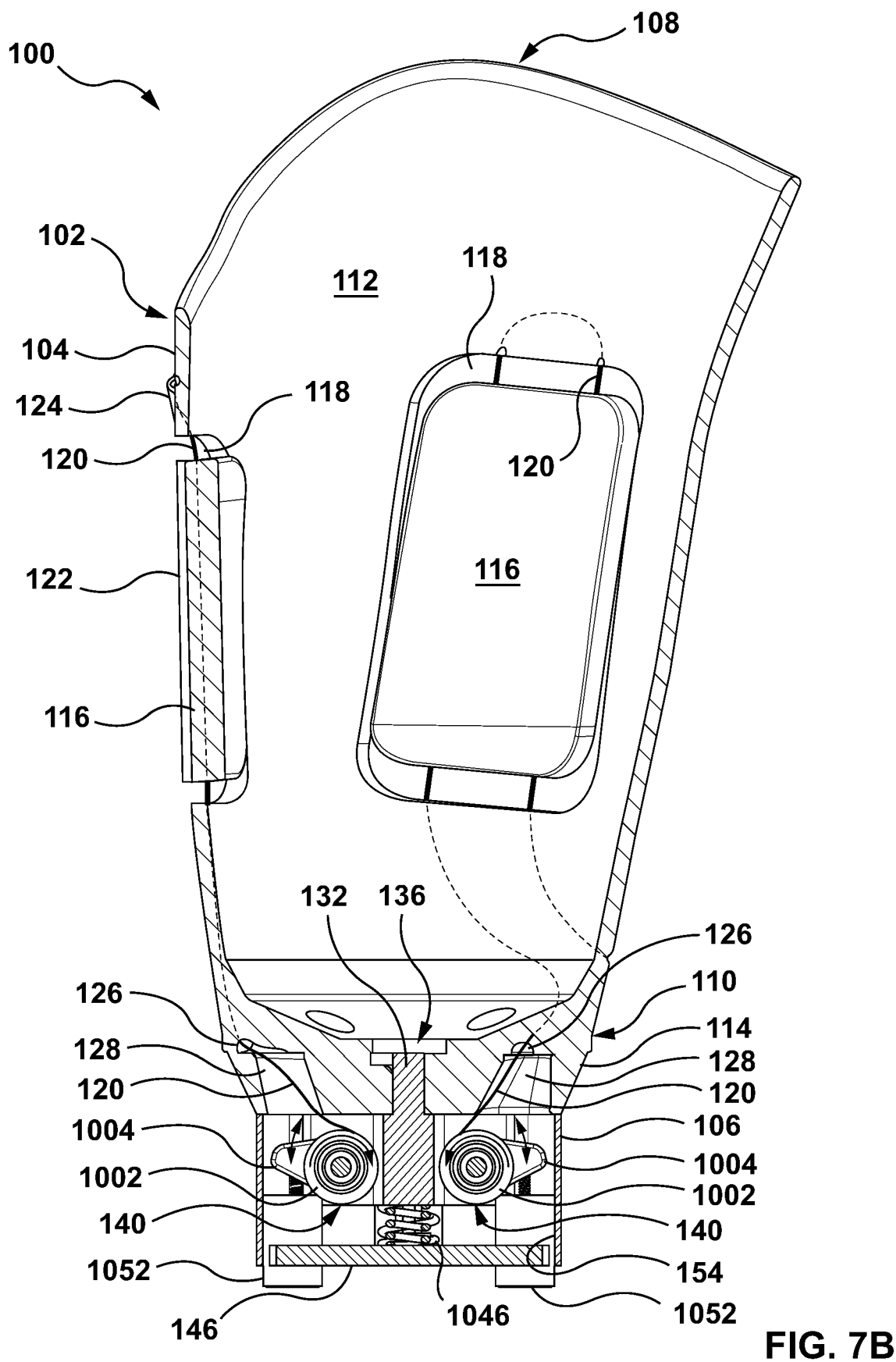
FIG. 7B is a cross-sectional view taken along the line 7-7 in FIG. 3, showing a second position of the panels of the self-adjusting socket of FIG. 1, when there is tension in the cables thereof.

Referring now primarily to FIGS. 7A and 7B, the self-adjusting socket 100 automatically tightens the panels 116 in the residuum receptacle 112 with each step taken by the user with the lower limb prosthesis, until a desired tightness is achieved. The term "step", as used herein, includes the act of lifting the lower limb prosthesis off of a surface and setting it down on the surface in different position with the user's weight applied, and also includes shifting the weight of the user's body off of and on to the lower limb prosthesis without lifting the lower limb prosthesis off of the surface. The self-adjusting socket 100 is configured to apply incremental tension across each panel 116 to move each panel 116 incrementally inwardly relative to the residuum receptacle 112. The incremental tension is applied by transmission of movement of the end effector of the lower limb prosthesis toward the residuum through a mechanical interface to a tensioner, with the resisted movement resulting from taking a step with (which includes shifting weight onto) the lower limb prosthesis. However, the movement from the step is transmitted to the tensioner only when the resistance of the mechanical interface exceeds a current tension applied by the tensioner, thereby preventing overtightening. Each step tightens the panels until the panels are tight enough.

In the illustrated embodiment, the tensioner applies tension to cables 120 that can be tightened or slackened. The term "cable" is used herein in its broadest sense, and includes not only braided metal rope, but also braided ropes formed from other materials, for example nylon paracord, as well as monofilament, for example fishing line, and any other suitable filar material.

Referring now to FIGS. 6, 6A, 6B and 6C, the cables 120 run through tubular cable tunnels 122 formed in the panels 116 and through covered cable guides 124 on the outer surface of the receptacle body 104. In alternative embodiments, the cable guides may be formed within the receptacle body. The cable guides 124 guide the cables 120 through the cable tunnels 122, with one end of each cable 120 being anchored to the housing 102, and the other end of each cable 120 passing through a respective port 126 into a respective passageway 128 through the mounting block 114 at the support end 110 of the receptacle body 104. The passageways 128 lead into the actuator enclosure 106, in which the tensioner is disposed. In the illustrated embodiment, the tensioner comprises a winch assembly 130, and the ends of the cables 120 that pass through the passageways 128 are coupled to the winch assembly 130, which is adapted to apply tension to, and release tension from, the cables 120. In alternate embodiments, both ends of each cable may be coupled to the winch assembly. The cable pathways shown in the figures are merely illustrative and not intended to be limiting; a wide array of cable pathways are possible, and may vary, for example, based on the number of panels and the position of those panels.

Figure 8A:
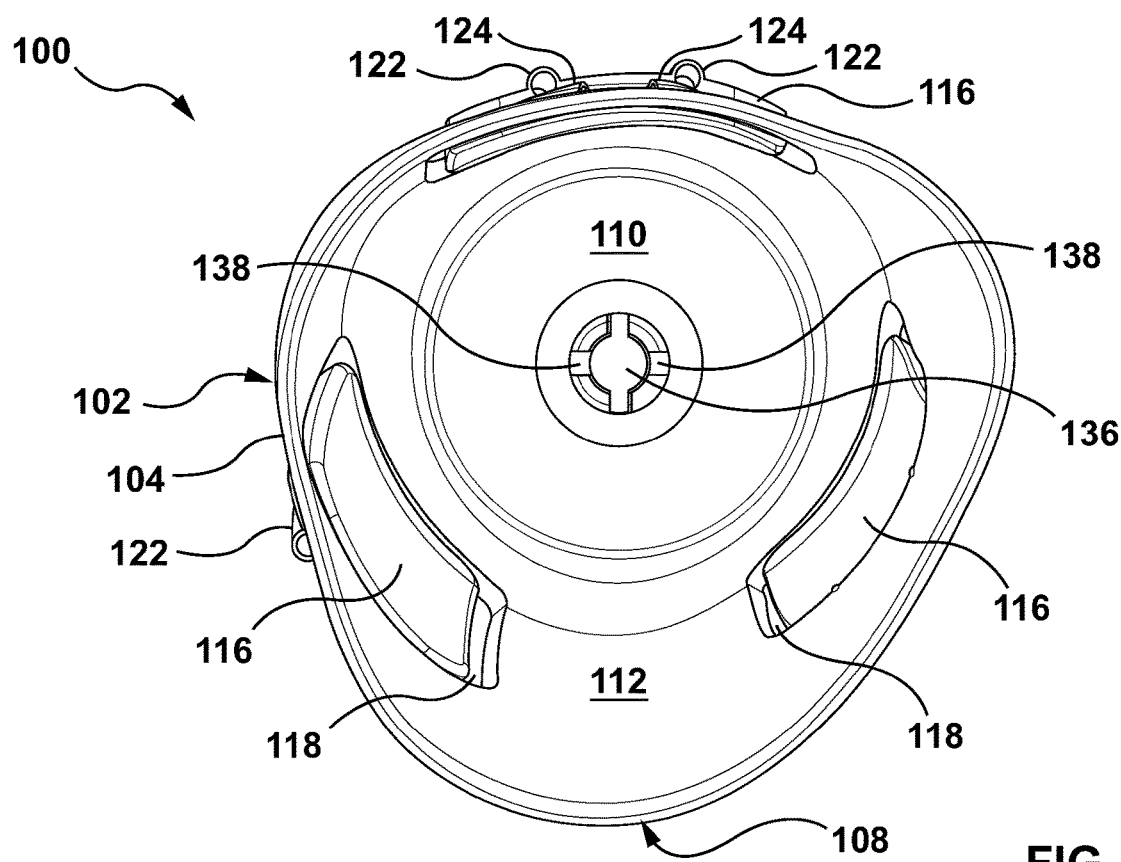
FIG. 8A is a top plan view of the self-adjusting socket of FIG. 1, showing the first position of the panels of the self-adjusting socket when there is slack in the cables thereof.
Figure 8B:
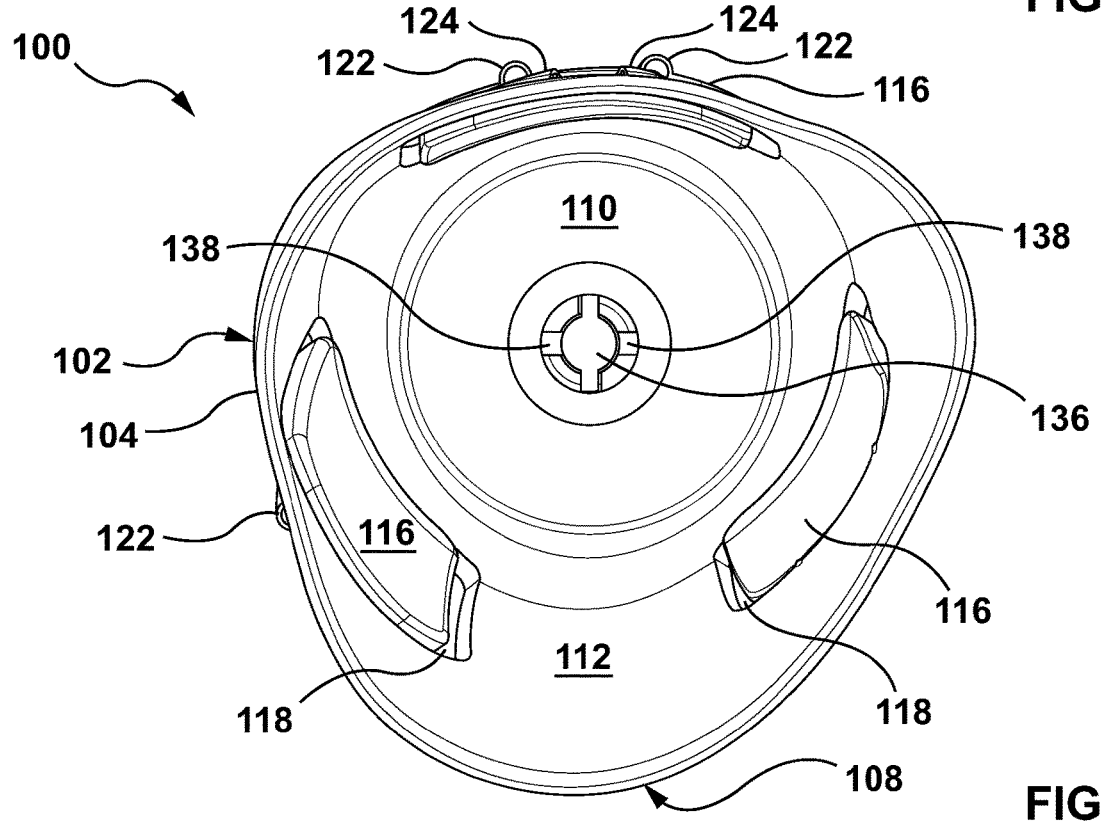
FIG. 8B is a top plan view of the self-adjusting socket of FIG. 1, showing the second position of the panels of the self-adjusting socket when there is tension in the cables thereof.

As can be seen in FIG. 7A, when there is slack in the cables 120, the panels 116 are held loosely within the respective openings 118, and will apply little or no pressure on the residuum. FIG. 8A shows the position of the panels 116 when there is slack in the cables 120, as seen from the open end 108 of the receptacle body 104. The shape (e.g. curvature) of the receptacle body 104, and the positioning of the cable tunnels 122 and cable guides 124, is such that as tension is applied and the cables 120 are tightened, the panels 116 are drawn inwardly into the openings 118, as shown in FIG. 7B, to apply pressure on the residuum. FIG. 8B shows the position of the panels 116, again from the open end 108 of the receptacle body 104, after the panels 116 have moved inwardly as a result of tightening the cables 120.

Figure 9:
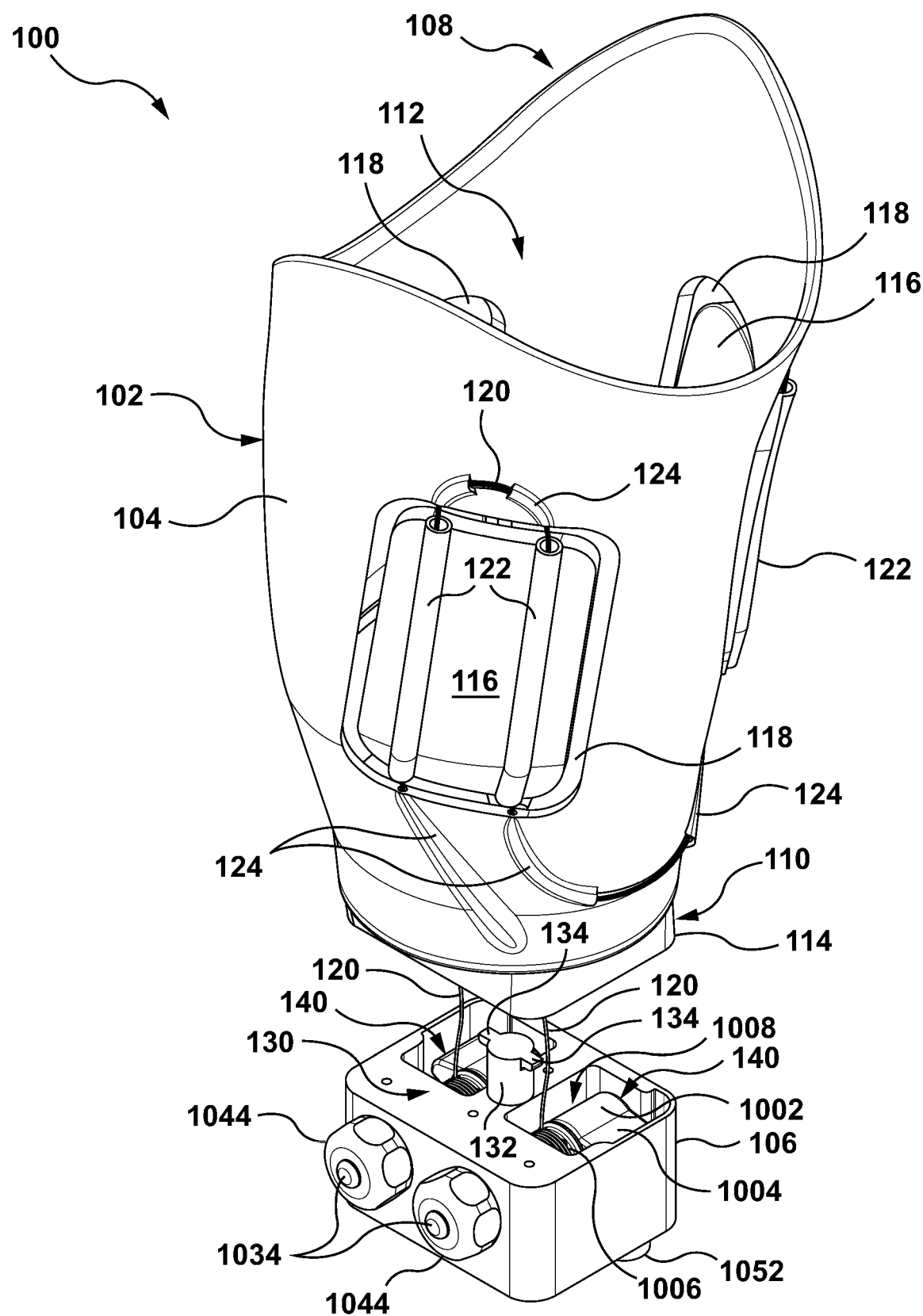
FIG. 9 is a top perspective view of the self-adjusting socket of FIG. 1 with an actuator enclosure thereof disengaged.
Figure 9A:
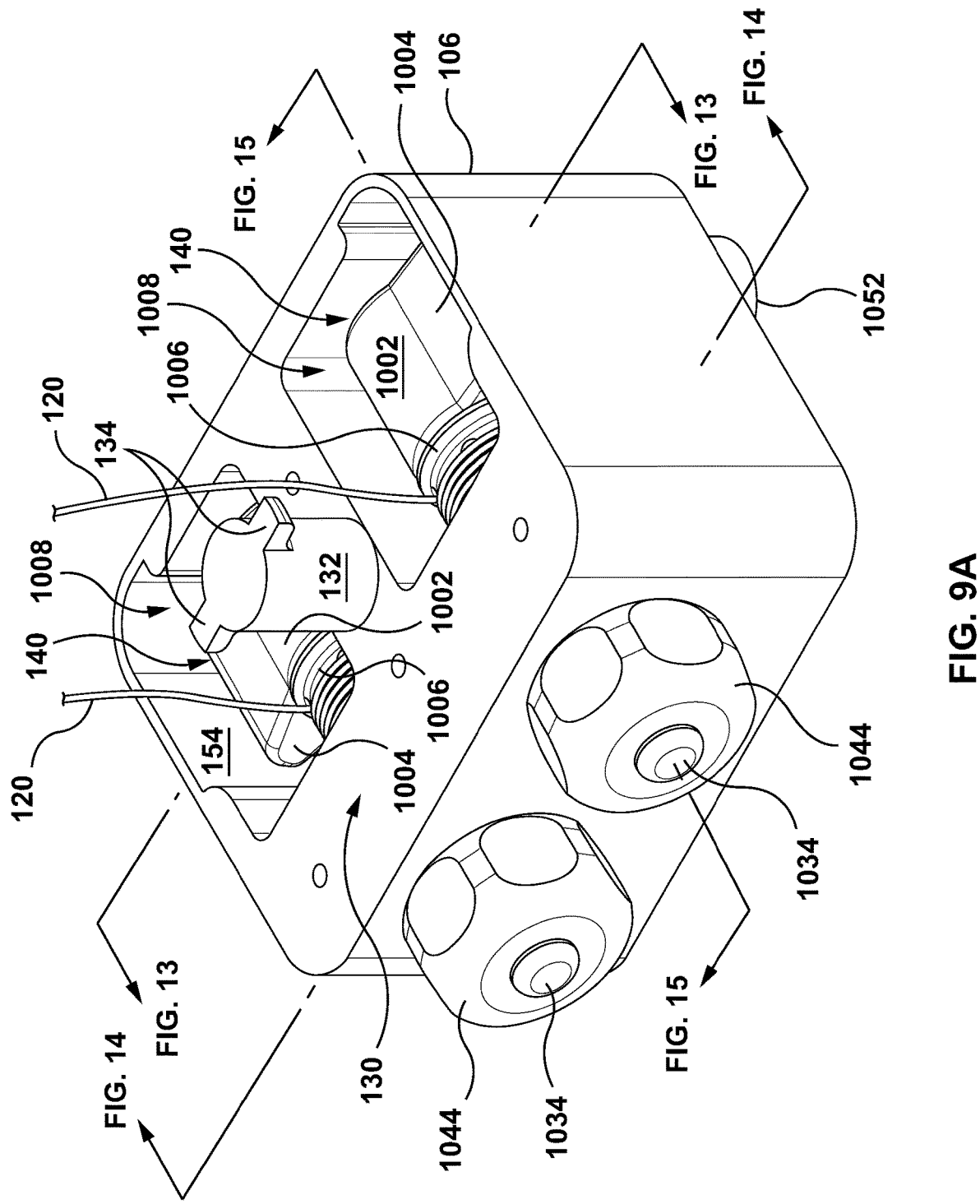
FIG. 9A is a top perspective view of the actuator enclosure of FIG. 9, including portions of a winch assembly contained therein.

As noted above, in the illustrated embodiment the actuator enclosure 106 is releasably mounted to the mounting block 114. More particularly, as can be seen in FIGS. 9 and 9A, in a preferred embodiment a locking post 132 having diametrically opposed locking lugs 134 extending outwardly therefrom stands proud of the actuator enclosure 106. The locking post 132 may be inserted through a correspondingly shaped locking aperture 136 (see FIGS. 8A and 8B) in the support end 110 of the receptacle body 104 and then twisted to engage the locking lugs with corresponding locking recesses 138 adjacent the locking aperture 136 (see FIGS. 8A and 8B) and secure the actuator enclosure 106 to the support end 110 of the receptacle body 104. By reversing this action, the actuator enclosure 106 may be disengaged from the support end 110 of the receptacle body 104, for example for maintenance.

Continuing to refer to FIGS. 9 and 9A, and as will be described in greater detail below, in the illustrated embodiment a pair of reciprocal actuators 140 are carried by the housing 102, in particular within the actuator enclosure 106; the reciprocal actuators 140 are coupled to the retention mechanism, which in the illustrated embodiment comprises the panels 116, by a mechanical linkage. In the illustrated embodiment, the reciprocal actuators 140 drive the winch assembly 130 carried by the actuator enclosure 106, and the mechanical linkage includes the tensioner that applies tension to the cables 120. Other types of mechanical linkage are also contemplated, for example suitable gearing. The reciprocal actuators 140 are configured to act through the mechanical linkage comprising the cables 120, via the winch assembly 130, to incrementally tighten the retention mechanism comprising the panels 116 against the residuum on each cycle of the reciprocal actuators 140. More particularly, each respective reciprocal actuator 140 is configured to incrementally increase tension in the respective cable 120 on each cycle of the respective reciprocal actuator 140, and incrementally increasing the tension in the respective cable 120 moves the respective panel(s) 116 incrementally inwardly relative to the residuum receptacle 120.

In the illustrated embodiment, the winch assembly 130 includes a releasable locking mechanism that is also carried by the housing 102, in particular within the actuator enclosure 106; the locking mechanism is configured to maintain the tightness of the retention mechanism comprising the panels 116 against the residuum after each cycle of the reciprocal actuator. An illustrative locking mechanism is described further below.

Each time a user takes a step with the lower limb prosthesis, that step transmits motion to a respective resilient resistive element coupled to a respective one of the reciprocal actuators 140. In the illustrated embodiment, the motion is transmitted by a movable platform 146 adapted to be coupled to an end effector and which is reciprocally movable toward and away from the residuum receptacle between a proximal position and a distal position. The resistance of the resistive elements is calibrated to a desired tightness of the retention mechanism comprising the panels 116; preferably the resistive elements are configured so that the resistance is adjustable and one such embodiment is described below. When the tightness of the retention mechanism comprising the panels 116 is below a desired threshold, each step transmits motion across the resistive elements to the reciprocal actuators 140 to cycle the reciprocal actuators 140. However, when the tightness of the retention mechanism comprising the panels 116 has reached the threshold, on each further step the resistive elements yield to absorb the motion, rather than transmitting the motion to the reciprocal actuators 140. When the resistive elements yield instead of transmitting motion, the reciprocal actuators 140 will fail to cycle on each further step, thereby inhibiting further tightening of the retention mechanism beyond the threshold.

Figure 10:
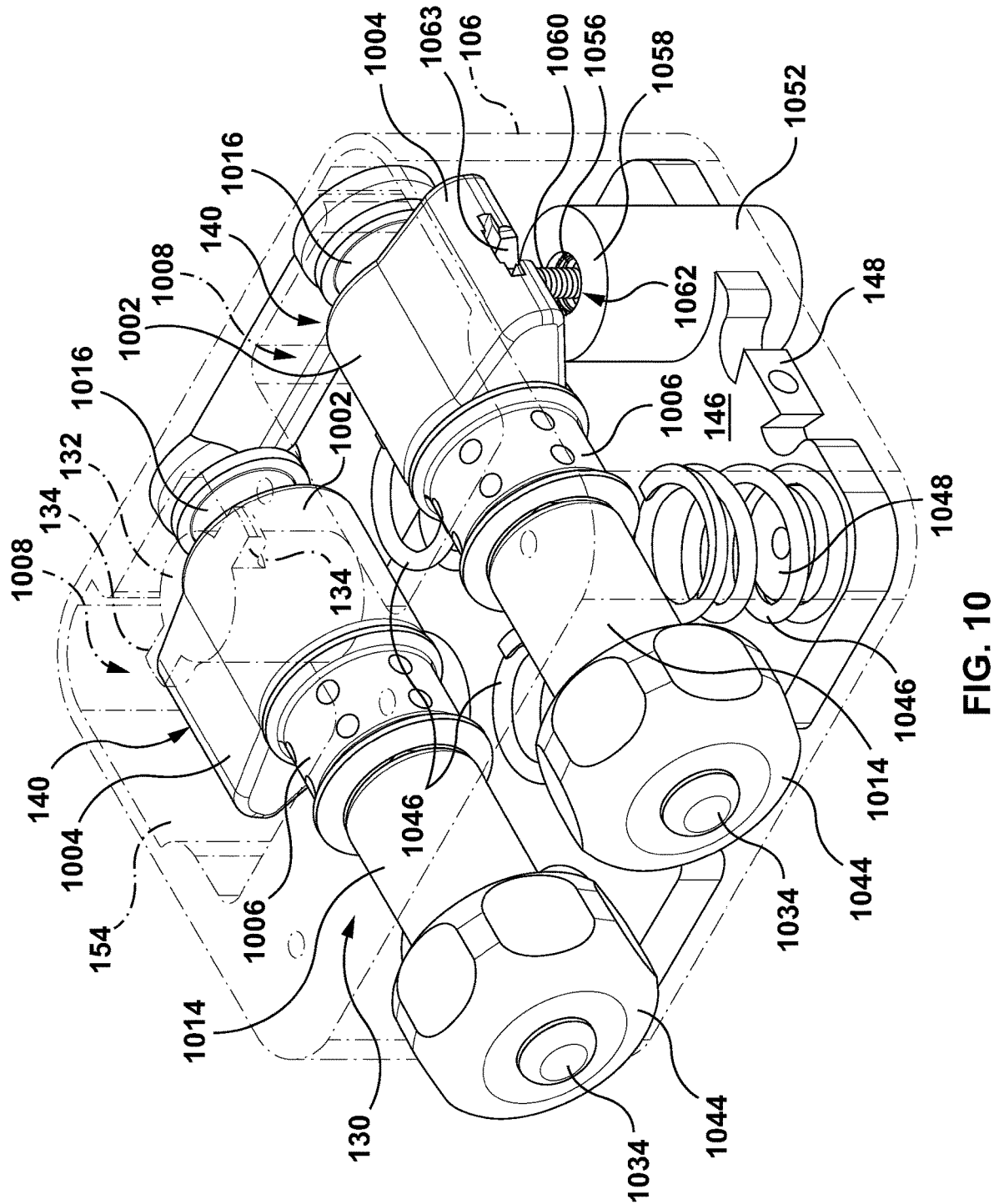
FIG. 10 is a transparent top perspective view of the actuator enclosure of FIG. 9, exposing the winch assembly and a movable platform.
Figure 11:
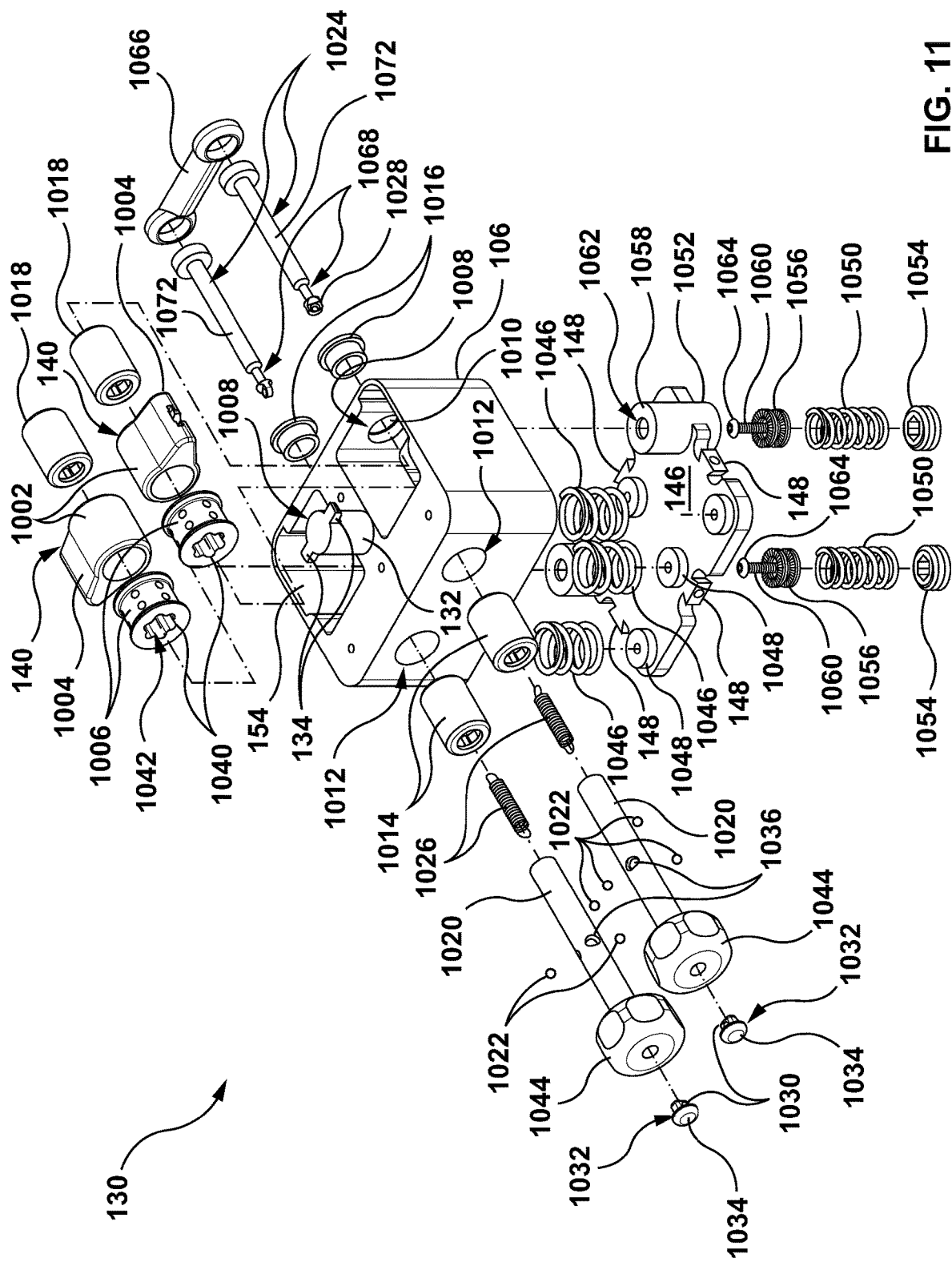
FIG. 11 is an exploded perspective view of the actuator enclosure, winch assembly and movable platform.
Figure 12:
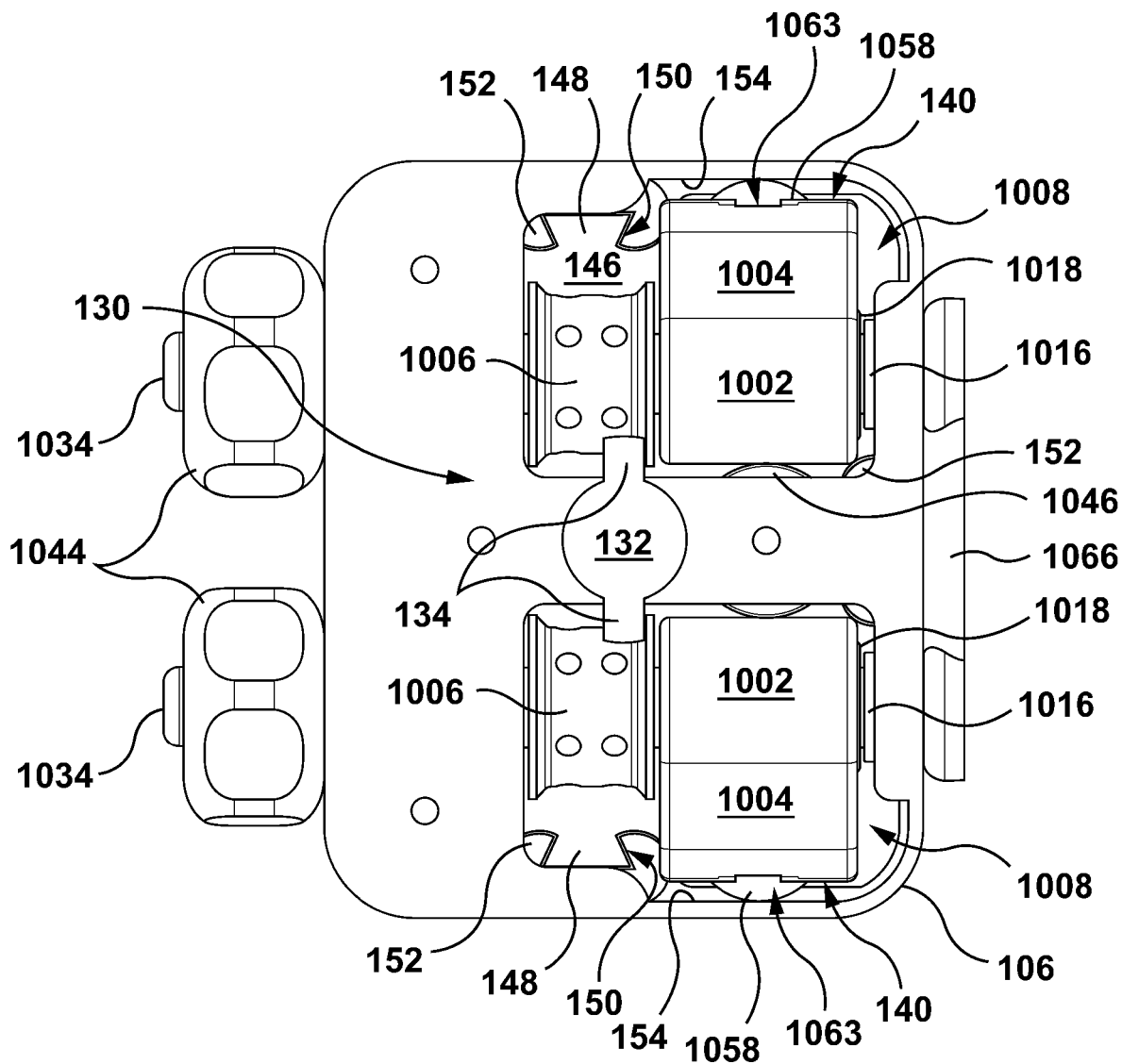
FIG. 12 is a top plan view of the actuator enclosure of FIG. 9, including portions of the winch assembly contained therein.

Reference is now made to FIGS. 10 to 12, which show, respectively, an assembled and an exploded view of the winch assembly 130 carried by the actuator enclosure 106, along with the movable platform 146. The actuator enclosure 106 functions as a winch body that carries the components of the winch assembly 130.

In the illustrated embodiment, the winch assembly comprises two reciprocal actuators 140, with each reciprocal actuator 140 comprising a rocker having a tubular cylindrical actuator body 1002 and an outwardly extending actuator arm 1004 that acts as a lever to pivot the reciprocal actuator 140 so that the reciprocal actuator 140 can rock back and forth about an axis extending through the actuator body 1002. The rocker is merely one non-limiting illustrative embodiment of a reciprocal actuator, and other types of reciprocal actuators are also contemplated.

Each of the reciprocal actuators 140 is coupled to a respective spool 1006 onto which the cables 120 may be wound and from which the cables 120 may be unwound to respectively tighten and loosen the retention mechanism comprising the panels 116. The reciprocal actuators 140 and the spools 1006 are disposed in respective winch cavities 1008 formed within the actuator enclosure 106. A bushing aperture 1010 is disposed at one end of each winch cavity 1008 and a bearing aperture 1012 is disposed at the opposite end of each winch cavity 1008, in registration with one another. A respective winch needle bearing 1014 with winch needle bearing rollers 1014R (FIGS. 15 and 16) is friction fit into each bearing aperture 1012, and a respective winch bushing 1016 is fitted into each bushing aperture 1010, so as to form two sets wherein the respective winch needle bearing 1014 and winch bushing 1016 are arranged coaxially with one another. The winch needle bearings 1014 are one-way needle bearings. Optionally, the winch bushings may be replaced with bearings.

In the illustrated embodiment, each reciprocal actuator 140 is coupled to its respective spool 1006 by way of an actuator needle bearing 1018, a hollow main winch shaft 1020, locking ball bearings 1022, and a release shaft 1024 disposed concentrically within the lumen of the hollow main winch shaft 1020. The actuator needle bearings 1018 are one-way needle bearings including actuator needle bearing rollers 1018R (FIGS. 15A and 15B), and are friction fit into the opening of the tubular cylindrical actuator body 1002. The main winch shafts 1020 each pass through a respective winch bushing 1016, respective actuator needle bearing 1018, and respective winch needle bearing 1014. The actuator needle bearings 1018 and the winch needle bearings 1014 are arranged so that the actuator needle bearing 1018 and the winch needle bearing 1014 on each main winch shaft 1020 have a common permitted direction of rotation; the permitted direction of rotation for each main winch shaft 1020 is opposite to that of the other main winch shaft 2020.

Each release shaft 1024 is axially movable within its respective main winch shaft 1020, and is coupled to the main winch shaft 1020 by a resilient member, in this case a helical extension spring which serves as a release spring 1026. More particularly, each release shaft 1024 terminates, at an end closest to the winch needle bearing 1014, with an eye 1028 adapted to receive a first hooked end of the respective release spring 1026. The other hooked end of the respective release spring 1026 is received in the eye 1030 of a spring retainer 1032. The eye 1030 of each spring retainer 1032 is disposed within the respective main winch shaft 1020, with the spring retainer 1032 being retained against the respective main winch shaft 1020 by an end cap 1034 of the spring retainer 1032. The locking ball bearings 1022 are received within respective locating apertures 1036 extending through the annular wall 1038 of the respective main winch shaft 1020. The locking ball bearings 1022 are forced outwardly by the release shaft 1024 and received within axially extending locking channels 1040 formed in the inner surface 1042 of the respective spool 1006. Because of the interengagement of the locking ball bearings 1022 with the locking channels 1040, rotation of the main winch shaft 1020 will result in rotation of the respective spool 1006.

Figure 13A:
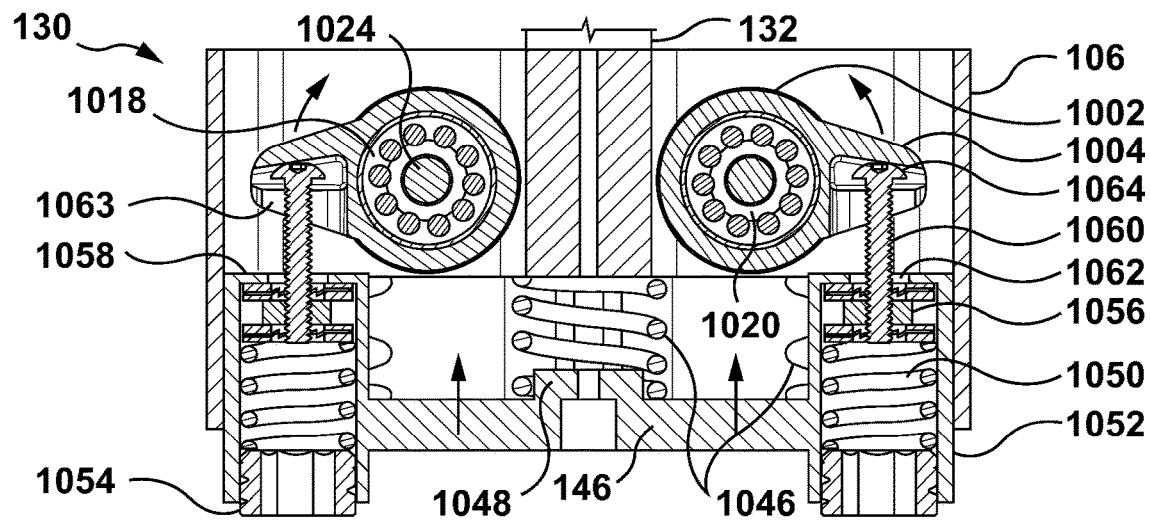
FIG. 13A is a cross-sectional view taken along the line 13-13 in FIG. 9A, showing actuator arms in a rest position with the movable platform in a distal position.
Figure 13B:
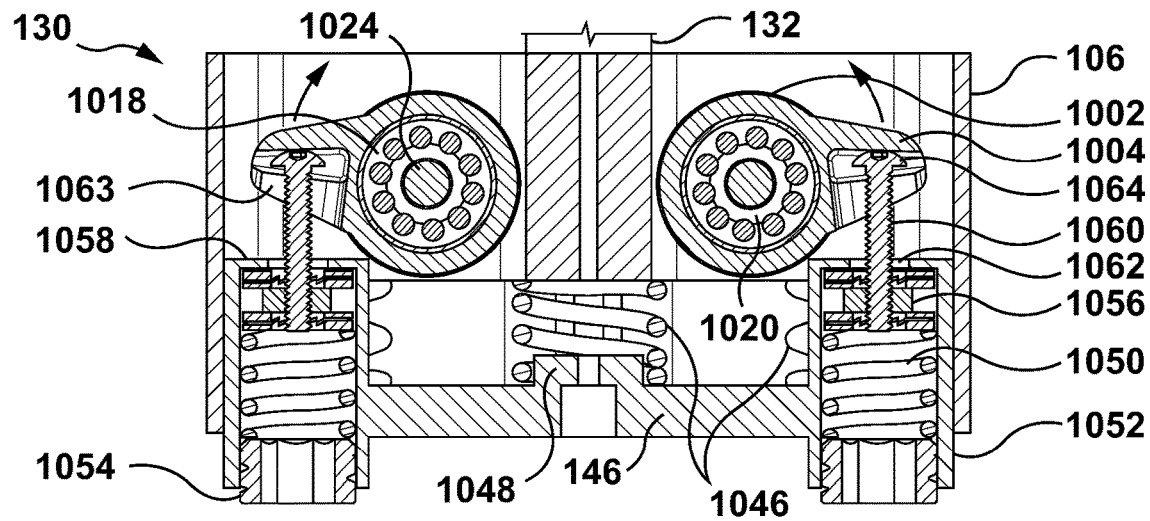
FIG. 13B is a cross-sectional view taken along the line 13-13 in FIG. 9A, showing the actuator arms in an actuated position with the movable platform in a proximal position.
Figure 13C:
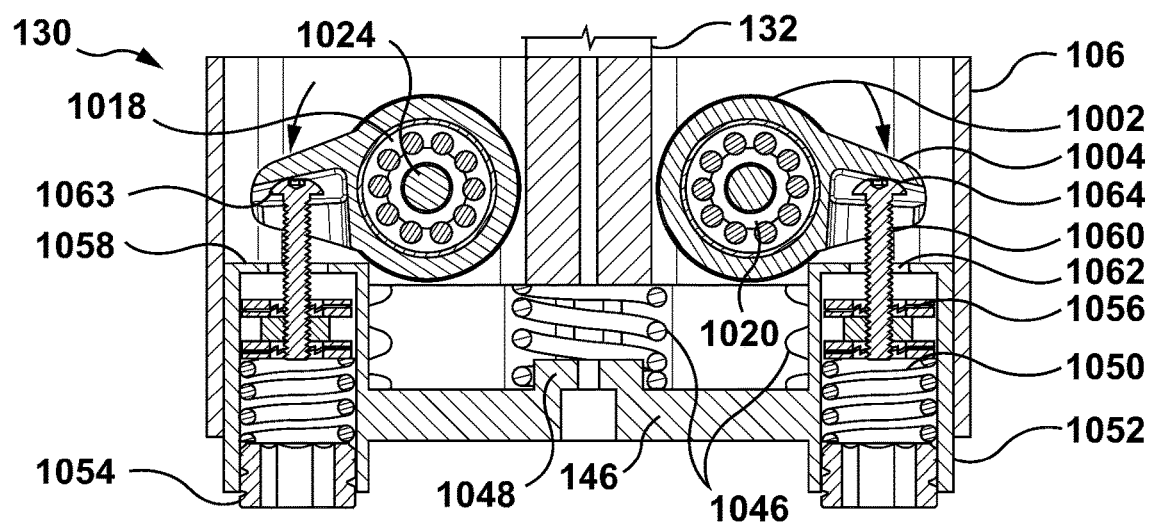
FIG. 13C is a cross-sectional view taken along the line 13-13 in FIG. 9A, showing the actuator arms in the rest position with the movable platform in the proximal position.
Figure 13A:
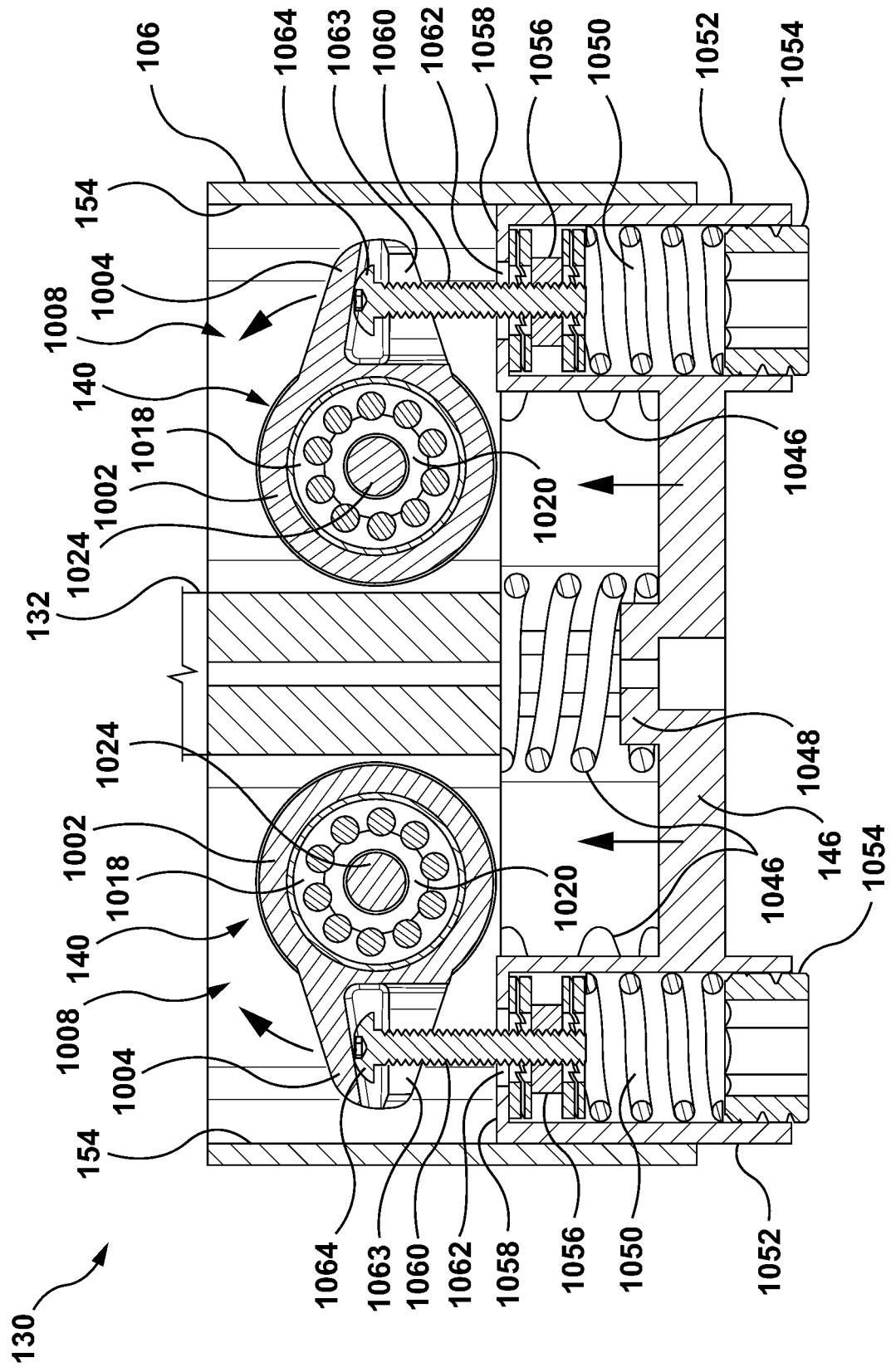
Figure 13B:
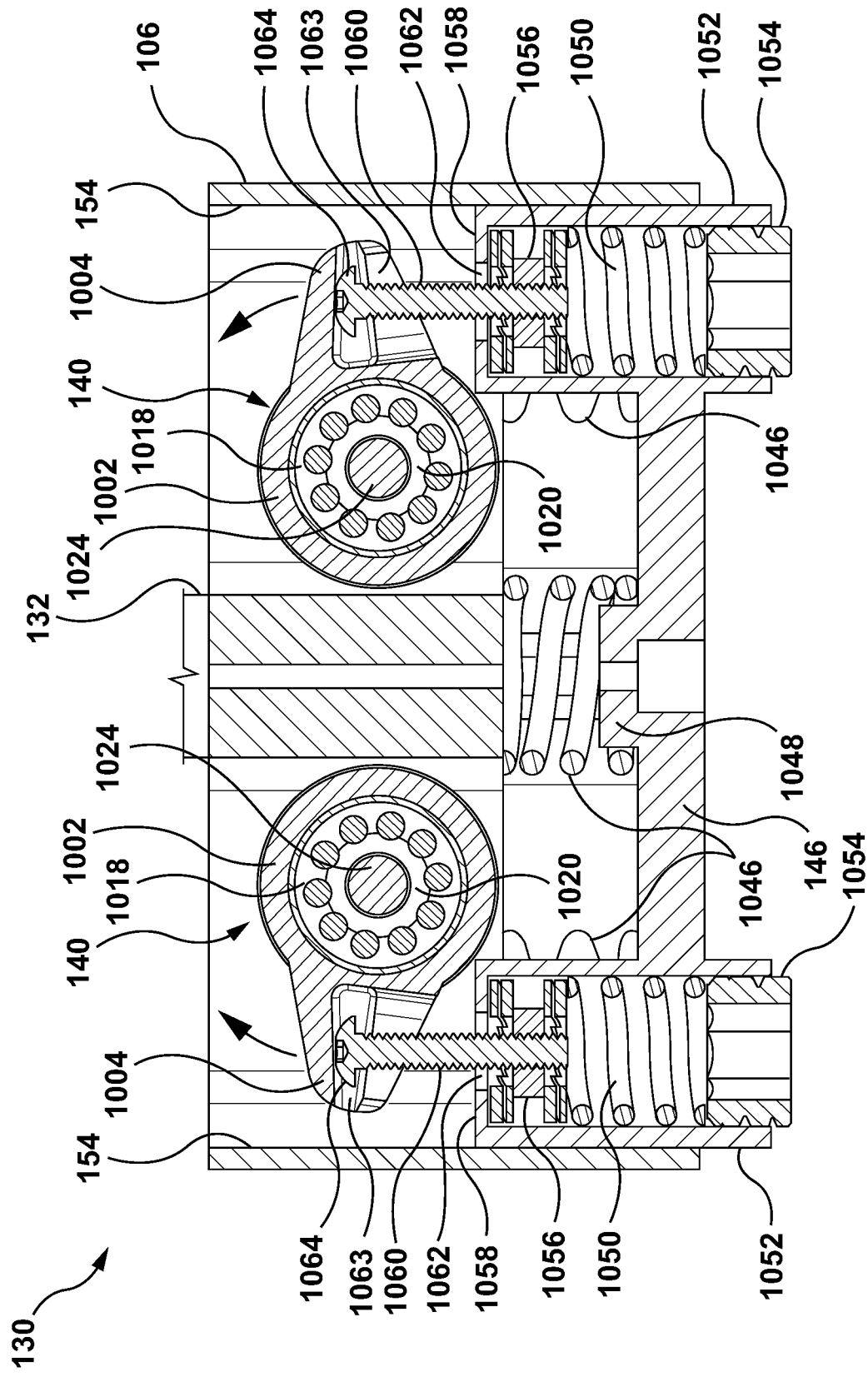
Figure 13C:
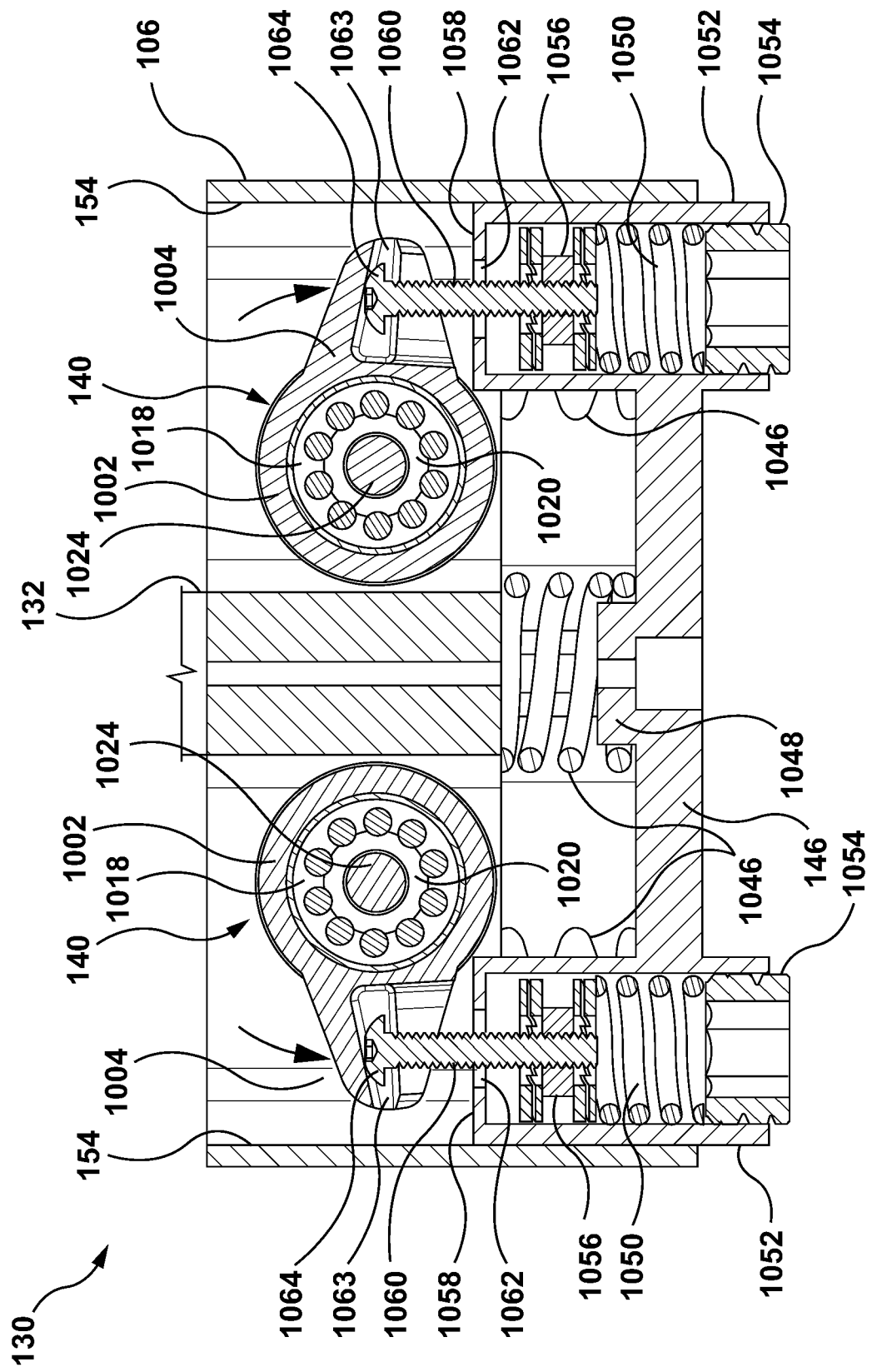

FIGS. 13A to 13C and 13AE to 13CE show various configurations of the actuator arms 140 and the movable platform 146. FIGS. 13A to 13C are positioned on the same page to facilitate comparison, and FIGS. 13AE to 13CE are respective enlargements of FIGS. 13A to 13C, each on a separate page to show more detail.

Reference is now made to FIGS. 13A and 13AE and to FIGS. 13B and 13BE, movement of the actuator arm 1004 from a rest position (see FIGS. 13A and 13AE) to an actuated position (see FIGS. 13B and 13BE) will rotate ("rock") the actuator body 1002 (clockwise on the left side of FIGS. 13A, 13AE, 13B and 13BE, anticlockwise on the right side of FIGS. 13A, 13AE, 13B and 13BE). Rotation of the actuator body 1002 is in the same rotational direction as the permitted direction of rotation of the respective actuator needle bearing 1018. Because the respective actuator needle bearing 1018 is friction fit within the actuator body 1002, the actuator needle bearing 1018 rotates along with the actuator body 1002. Since the actuator needle bearing 1018 is rotating in the same rotational direction that the main winch shaft 1020 is permitted to rotate within the actuator needle bearing 1018, this is equivalent to attempted rotation of the main winch shaft 1020 opposite to the permitted direction of rotation within the actuator needle bearing 1018. As a result, the actuator needle bearing 1018 binds on the main winch shaft 1020 so that rotation of the actuator body 1002 drives rotation of the main winch shaft 1020 (clockwise on the left side of FIGS. 13A, 13AE, 13B and 13BE, anticlockwise on the right side of FIGS. 13A, 13AE, 13B and 13BE). Since the actuator needle bearing 1018 and the winch needle bearing 1014 on each main winch shaft 1020 have a common permitted direction of rotation, the main winch shaft 1020 can rotate within the winch needle bearing 1014 until the actuator arm 1004 reaches the actuated position (see FIGS. 13B and 13BE). The permitted direction of rotation is in a winding direction of the respective spool 1006, so the movement of the actuator arm 1004 from the rest position (see FIGS. 13A and 13AE) to the actuated position (see FIGS. 13B and 13BE) will incrementally rotate the respective main winch shaft 1020 and the respective spool 1006 coupled thereto in a winding direction of the respective spool 1006. This incrementally winds the respective cable 120 further onto the respective spool 1006 and incrementally increases the tension in the respective cable 120. Rotation in the unwinding direction of the respective spool 1006 is resisted by the respective winch needle bearing 1014 so that tension on the respective cable 120 is maintained.

From the actuated position shown in FIGS. 13B and 13BE, the actuator arm 1004 can reciprocate back to the rest position shown in FIGS. 13A and 13AE, thereby rotating the actuator body 1002 back in the opposite rotational direction (anticlockwise on the left side of FIGS. 13A, 13AE, 13B and 13BE, clockwise on the right side of FIGS. 13A, 13AE, 13B and 13BE). This rotation of the actuator body 1002 and the respective actuator needle bearing 1018 therein is in the opposite rotational direction to the permitted direction of rotation of the respective actuator needle bearing 1018, which is equivalent to rotation of the main winch shaft 1020 in the permitted direction of rotation within the actuator needle bearing 1018. As a result, the actuator needle bearing 1018 and the actuator body 1002 can slip over the main winch shaft 1020 until the actuator arm 1004 returns to the rest position shown in FIGS. 13A and 13AE. At the same time, because rotation of the actuator body 1002 and the respective actuator needle bearing 1018 therein is in the opposite rotational direction to the common permitted direction of rotation of the respective winch needle bearing 1014, the winch needle bearing 1014 will inhibit the main winch shaft 1020 from rotating back with the respective actuator body 1002 and the respective actuator needle bearing 1018. Thus, each cycle of the reciprocal actuator 140 from the rest position (FIGS. 13A and 13AE) to the actuated position (FIGS. 13B and 13BE) and back to the rest position (FIGS. 13A and 13AE) will incrementally rotate (index) the respective main winch shaft 1020. Since rotation of the main winch shaft 1020 will result in rotation of the respective spool 1006 by way of interengagement of the locking ball bearings 1022 with the locking channels 1040, each cycle of the reciprocal actuator 140 from the rest position (FIGS. 13A and 13AE) to the actuated position (FIGS. 13B and 13BE) and back to the rest position (FIGS. 13A and 13AE) will incrementally rotate (index) the spool 1006. Thus, each cycle of the reciprocal actuator 140 indexes the spool 1006 to wind the respective cable 120 onto the spool 1006 to incrementally increase the tension in the respective cable 120.

Reference is again made to FIGS. 10 to 12. In the illustrated embodiment, each main winch shaft 1020 terminates with a respective manual tensioning knob 1044 at the end of the main winch shaft 1020 that receives the spring retainer 1032. Preferably the manual tensioning knob 1044 is monolithically formed as part of the main winch shaft 1020; in other embodiments it may be a separate part affixed to the main winch shaft. By rotating the manual tensioning knob 1044 in the permitted direction of rotation, the main winch shaft 1020 and hence the spool 1006 may be rotated independently of the actuator 140 to manually apply tension to the cables 120. Thus, the manual tensioning knobs 1044 provide a manual tightening mechanism for tightening the retention mechanism.

As noted above, in the illustrated embodiment, motion from steps taken with the prosthesis is transmitted to the reciprocal actuators 140 by a movable platform 146. Referring again to FIGS. 10 and 11, in the illustrated embodiment the movable platform 146 is carried by the housing 102, in particular by the actuator enclosure 106. The four edges of the movable platform 146 each include a recessed dovetail guide follower 148 which is received in a respective correspondingly shaped guide channel 150 (see FIGS. 6, 6C and 12) formed in a respective elongate inward projection 152 on a respective interior sidewall 154 of the actuator enclosure 106 (see FIG. 12). The platform 146 is reciprocally movable toward and away from the residuum receptacle 112 between a distal position (see FIGS. 13A and 13AE) and a proximal position (see FIGS. 13B and 13C). The platform 146 is closer to the residuum receptacle 112 in the proximal position than in the distal position. As can be seen in FIGS. 8A and 8B, the reciprocal actuators 140 are carried by the housing 102, in particular the actuator enclosure 106, between the residuum receptacle 112 and the platform 146. Thus, in the illustrated embodiment the platform 146 is movable toward and away from the main winch shafts 1020 and the spools 1006, and is closer to the main winch shafts 1020 and the spools 1006 in the proximal position than in the distal position. The platform is biased into the distal position, for example by one or more biasing members.

In the illustrated embodiment, the platform is biased into the distal position by a plurality of cushioning springs 1046 in the form of spaced-apart helical compression springs that are secured on respective locating studs 1048 on the platform 146 and received in corresponding spring recesses in the actuator enclosure 106. Other types of compression springs may also be used. The cushioning springs 1046 may be used, alone or in cooperation with other components, to couple the platform 146 to the actuator enclosure 106. In other embodiments, the platform may be biased into the distal position by a single centrally disposed spring, such as a centrally disposed bellows spring.

Each time a user takes a step with the lower limb prosthesis, when the user puts weight on the end effector (not shown) coupled to the platform 146, the weight will overcome the bias applied by the cushioning springs 1046 and move the platform 146 from the distal position into the proximal position. This movement of the platform 146 in turn transmits movement to a pair of resistive elements 1050 trapped between the platform 146 and the reciprocal actuators 140, with each resistive element 1050 coupled to the actuator arm 1004 of a respective one of the reciprocal actuators 140.

In the illustrated embodiment, the resistive elements 1050 are helical compression springs, although this is merely an illustrative example and is not limiting; other types of resistive elements may also be used. The platform 146 carries a pair of opposed hollow cylinder barrels 1052, each of which is positioned in registration with a respective one of the actuator arms 1004. One of the resistive elements 1050 is disposed in each one of the cylinder barrels 1052, and each cylinder barrel 1052 is threaded at its bottom to receive a setscrew 1054 that functions as a cylinder cap. A respective piston 1056 is trapped in each cylinder barrel 1052, between the respective resistive element 1050 and the head 1058 of the respective cylinder barrel 1052 opposite the setscrew 1054. Each piston 1056 carries a piston rod 1060 that projects through a rod aperture 1062 in the head 1058 of the respective cylinder barrel 1052 and terminates in a piston rod connector 1064 which is coupled to a respective one of the actuator arms 1004. In the illustrated embodiment, bolts are used as the piston rods 1060 with the bolt heads functioning as the piston rod connectors 1064. The actuator arms 1004 each include an elongate T-shaped slot 1063 that receives a respective one of the piston rod connectors 1064 such that axial movement of the piston 1056 within the respective cylinder barrel 1052 will cause the respective piston rod 1060 to pull or push the actuator arm 1004. Thus, movement of the piston 1056 and with it the piston rod 1060 can drive movement of the respective actuator arm 1004 between the rest position (FIGS. 13A and 13AE) and the actuated position (FIGS. 13B and 13BE). The use of bolts as piston rods is merely an illustrative embodiment and is not limiting. For example, and without limitation, in other embodiments, the piston rod connector may be a clevis assembly, or a hook, or an eye. The coupling of the piston rod connectors 1064 to the actuator arms 1004, in cooperation with the cushioning springs 1046, couples the platform 146 to the actuator enclosure 106. Other couplings between the platform 146 and the actuator enclosure 106 are also contemplated.

Reference is now made to FIGS. 13A through 13C and 13AE through 13CE. FIGS. 13A and 13AE show the actuator arms 1004 in the rest position with the platform 146 in the distal position; FIGS. 13B and 13BE show the actuator arms 1004 in the actuated position with the platform 146 in the proximal position, and FIGS. 13C and 13CE show the actuator arms 1004 in the rest position with the platform 146 in the proximal position.

FIGS. 13A and 13AE represent the configuration of the winch assembly 130 when a user is not applying weight to the end effector, for example when the user is walking and the end effector has yet to engage the surface (e.g. ground or floor) upon which the user is walking, or if the user's weight is on the alternate lower limb. When the user applies weight to the end effector, the winch assembly 130 will move to either the configuration in FIGS. 13B and 13BE, or to the configuration in FIGS. 13C and 13CE, depending on the tension in the cables 120. When the user applies weight to the end effector, the force applied by the weight of the user overcomes the resistance of the cushioning springs 1046, causing the platform 146 to move from the distal position (FIGS. 13A and 13AE) into the proximal position (FIGS. 13B and 13BE and FIGS. 13C and 13CE). This movement of the platform 146 applies force to the resistive elements 1050 via the setscrews 1054, since each resistive element 1050 is trapped in the respective cylinder barrel 1052 between the respective setscrew 1054 and the respective piston 1056, which is movable within the respective cylinder barrel 1052. As the platform 146 moves from the distal position (FIGS. 13A and 13AE) into the proximal position (FIGS. 13B and 13BE and FIGS. 13C and 13CE), the respective resistive element 1050 will either act as a rigid body bracing the respective piston 1056 against the head 1058 of the respective cylinder barrel 1052 (FIGS. 13B and 13BE), or yield against the respective piston 1056 (FIGS. 13C and 13CE), depending on whether the resistance to movement of the respective piston 1056 is greater than the resistance to further compression of the respective resistive element 1004. Because the respective piston 1056 engages the respective actuator arm 1004, the resistance to movement of the respective piston 1056 depends on the resistance to movement of the respective actuator arm 1004. Movement of the respective actuator arm 1004 rotates the respective actuator body 1002, which in turn rotates the main winch shaft 1020 and the spool 1006 to further wind the respective cable 120 onto the spool 1006 to incrementally increase the tension in the respective cable 120. Therefore, the resistance to movement of the respective piston 1056 depends on the tension in the respective cable(s) 120.

More particularly, the respective piston 1056 cannot move with the platform 146 as the platform 146 moves into the proximal position unless the respective actuator arm 1004 can move into the actuated position by rotating the respective actuator body 1002 to pivot the respective reciprocal actuator 140. But the respective reciprocal actuator 140 is bound to the respective main winch shaft 1020 by the respective one-way actuator needle bearing 1018, so the respective reciprocal actuator 140 cannot pivot unless the respective main winch shaft 1020 can rotate. Since the respective main winch shaft 1020 is fixed to the spool 1006, the respective main winch shaft 1020 cannot rotate unless the spool 1006 can also rotate. Since the respective cable 120 is wound onto the respective spool 1006 and is under tension, rotation of the respective spool 1006 requires that the existing tension in the respective cable 120 be overcome. Thus, the tension in the respective cable 120 propagates back through the respective spool 1006, main winch shaft 1020 and actuator needle bearing 1018 to resist pivoting of the respective reciprocal actuator 140, thereby resisting movement of the actuator arm 1004 from the rest position to the actuated position and providing the resistance to movement of the respective piston 1056.

Because the tension in the cables 120 tightens the panels 116 against the residuum, the amount of tension in the cables 120 corresponds to the tightness of the retention mechanism comprising the panels 116. If the tension in the cables 120 is below a threshold, when the end effector engages the surface, the winch assembly 130 will move to the configuration in FIGS. 13B and 13BE, which will increase tension in the cables 120. However, when the tension in the cables 120 is at or above the threshold, when the end effector engages the surface the winch assembly 130 will move to the configuration in FIGS. 13C and 13CE, which will not increase the tension in the cables 120. The threshold for the tension in the cables 120 corresponds to the resistance of the resistive elements 1050, which may be adjusted by tightening or loosening the respective setscrew 1054 so that the threshold is adjustable. Moreover, the resistance of the respective resistive elements 1050 need not be identical.

Figure 14:
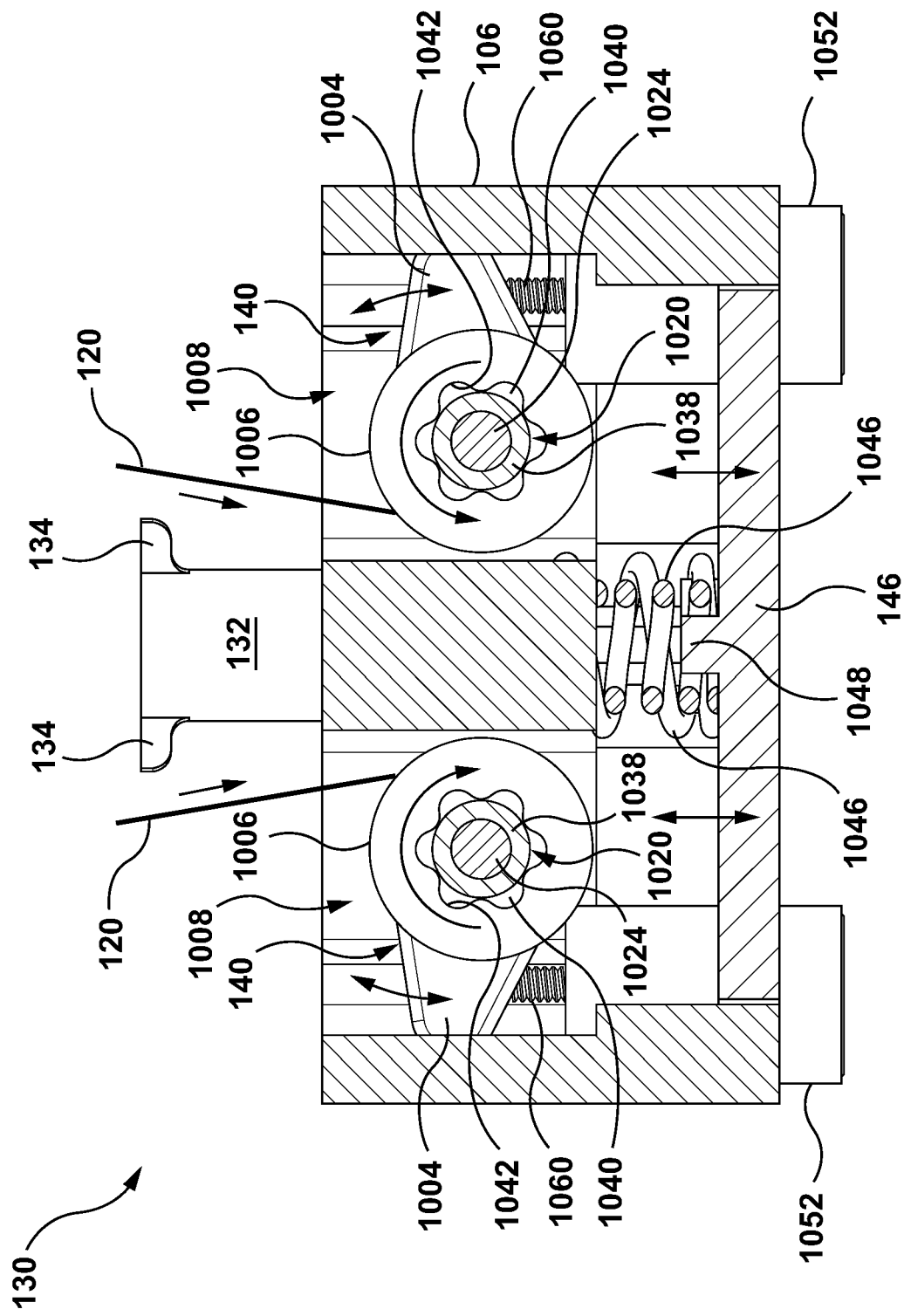
FIG. 14 is a cross-sectional view taken along the line 14-14 in FIG. 9A.

Reference is first made to FIGS. 13B and 13BE, which illustrate the scenario where the tension in the cables 120 is below the threshold. In other words, in the scenario shown in FIGS. 13B and 13BE, the amount of force required to further compress the respective resistive element 1050 exceeds the resistance to movement of the respective piston 1056 resulting from the tension in the corresponding cable 120. Therefore, the respective resistive element 1050 does not compress, and instead acts as a rigid body that braces the respective piston 1056 against the setscrew 1054, so that movement of the platform 146 toward the reciprocal actuator 140 will drive the piston rod 1060 into the actuator arm 1004 to move the actuator arm 1004 into the actuated position and rotate the actuator body 1002. This in turn rotates the main winch shaft 1020 and the spool 1006 to further wind the respective cable 120 onto the spool 1006 to incrementally increase the tension in the respective cable 120. Thus, where the tension in the cables 120 is below the threshold, movement of the platform 146 toward the proximal position pushes the respective resistive element 1050 toward the reciprocal actuator 140 whereby the respective resistive element 1050 transmits the movement of the platform 146 via the piston 1056 and piston rod 1060 to the actuator arm 1004 to pivot the reciprocal actuator 140 and thereby index the spool 1006. Accordingly, when the tightness of the retention mechanism comprising the panels 116 and cables 120 is below a desired threshold, each step transmits motion across the resistive elements 1050 to the reciprocal actuators 140 to cycle the reciprocal actuators 140. FIG. 14 shows how each movement of the respective actuator arm 1004 into the actuated position rotates the respective actuator body 1002, which (via the actuator needle bearing 1018, not shown in FIG. 14) rotates the respective main winch shaft 1020 and thereby rotates the respective spool 1006 to wind the respective cable 120 onto the spool 1006 to incrementally increase the tension in the cable 120.

Reference is now made to FIGS. 13C and 13CE, which illustrate the scenario where the tension in the cables 120 is at or above the threshold. In the scenario shown in FIGS. 13C and 13CE, the amount of force required to further compress the respective resistive element 1050 is less than the resistance to movement of the respective piston 1056 resulting from the tension in the corresponding cable 120 transmitted back to the respective actuator arm 1004. In other words, more force is required to overcome the tension in the respective cable 120 and move the actuator arm 1004 from the rest position to the actuated position than is required to further compress the respective resistive element 1050. Therefore, instead of movement of the platform 146 being transmitted through the respective resistive element 1050 to move the respective piston 1056 and pivot the respective reciprocal actuator 140, the respective resistive element 1050 acts like a spring rather than a rigid body, and is compressed between the respective setscrew 1054 and the respective piston 1056 as the platform 146 moves. In other words, the resistance of the respective resistive element 1050 cannot overcome the tension in the respective cable 120, so the resistive element 1050 yields (e.g. the spring is compressed). Accordingly, instead of the piston rod 1060 moving the actuator arm 1004 toward the actuated position, the actuator arm 1004 is maintained in position by the tension in the cable 120 and the respective piston 1056 is pushed into the cylinder barrel 1052, where it compresses the respective resistive element 1050 against the respective setscrew 1054. Thus, when the tightness of the retention mechanism comprising the panels 116 has reached the threshold, on each further step the resistive elements 1050 yield to absorb the motion of the platform 146, rather than transmitting the motion of the platform 146 to the reciprocal actuators 140. When the resistive elements 1050 yield instead of transmitting motion, the reciprocal actuators 140 will fail to cycle on each further step, thereby inhibiting further tightening of the retention mechanism beyond the threshold.

When the user removes the weight from the end effector, the cushioning springs 1046 return the platform 146 from the proximal position (FIGS. 13B and 13BE and FIGS. 13CE) to the distal position (FIGS. 13A and 13AE).

Accordingly, as has been shown with respect to FIGS. 13A through 13C and FIGS. 13AE through 13CE, reciprocal movement of the platform 146 into the proximal position and back to the distal position cycles the reciprocal actuators 140 only where the resistance to compression of the respective resistive element 1050 exceeds the resistance to movement of the respective reciprocal actuator 140 resulting from the tension in the respective cable 120 so that the respective resistive element 1050 transmits the movement of the platform 146 to the respective reciprocal actuator 140 instead of yielding to the movement of the platform 146.

Thus, in the illustrated embodiment, the resistive element 1050, reciprocal actuator 140 and actuator needle bearing 1018 provide a mechanical interface to transmit movement of the end effector of the lower limb prosthesis toward the residuum from a step to a tensioner comprising the main winch shaft 1020, release shaft 1024, locking ball bearings 1022, and spool 1006, with resistance of the mechanical interface provided by the resistive element 1050 (e.g. a spring).

Figure 15A:
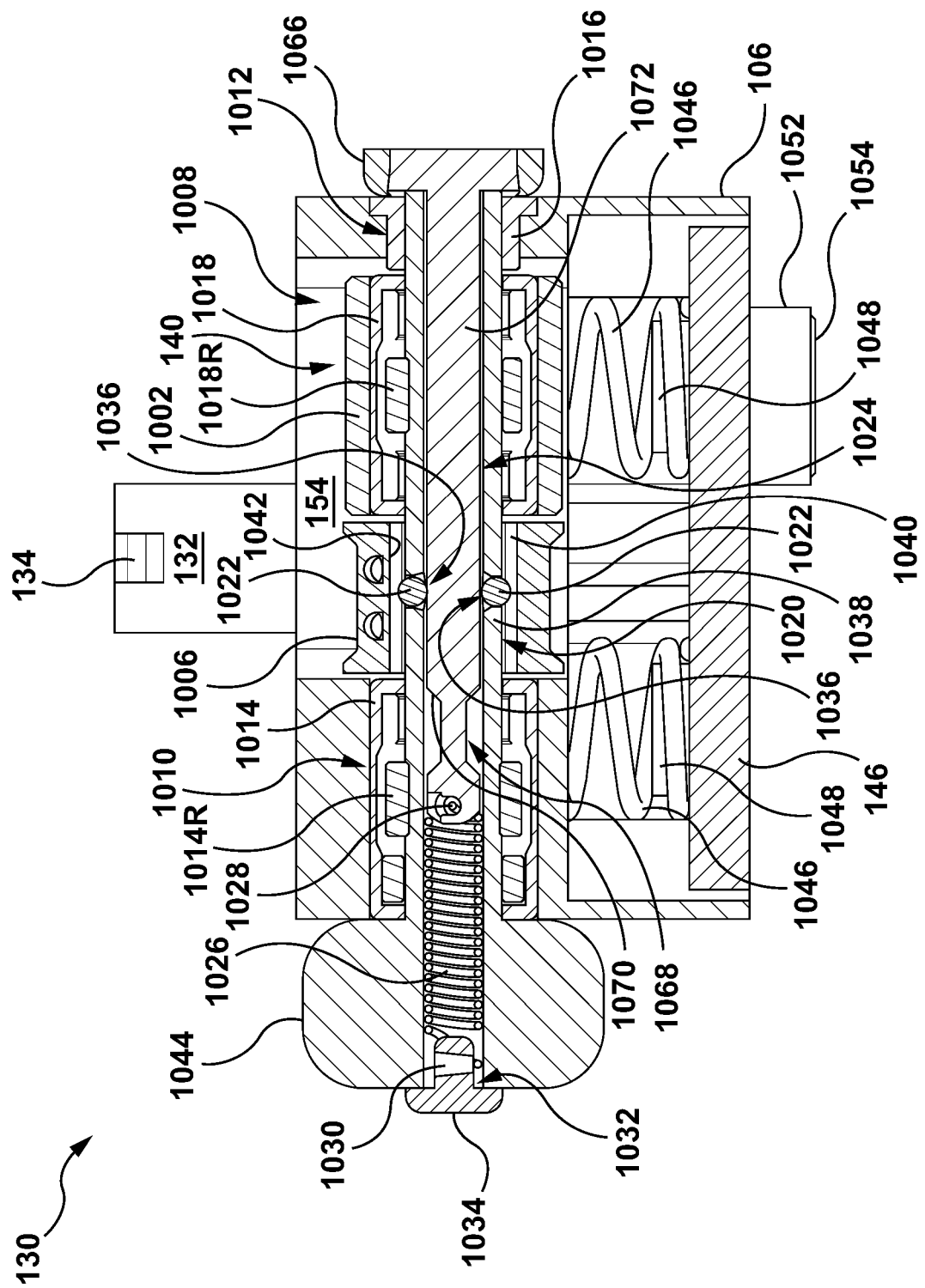
FIGS. 15A and 15B are cross-sectional views taken along the line 15-15 in FIG. 9A.
Figure 15B:
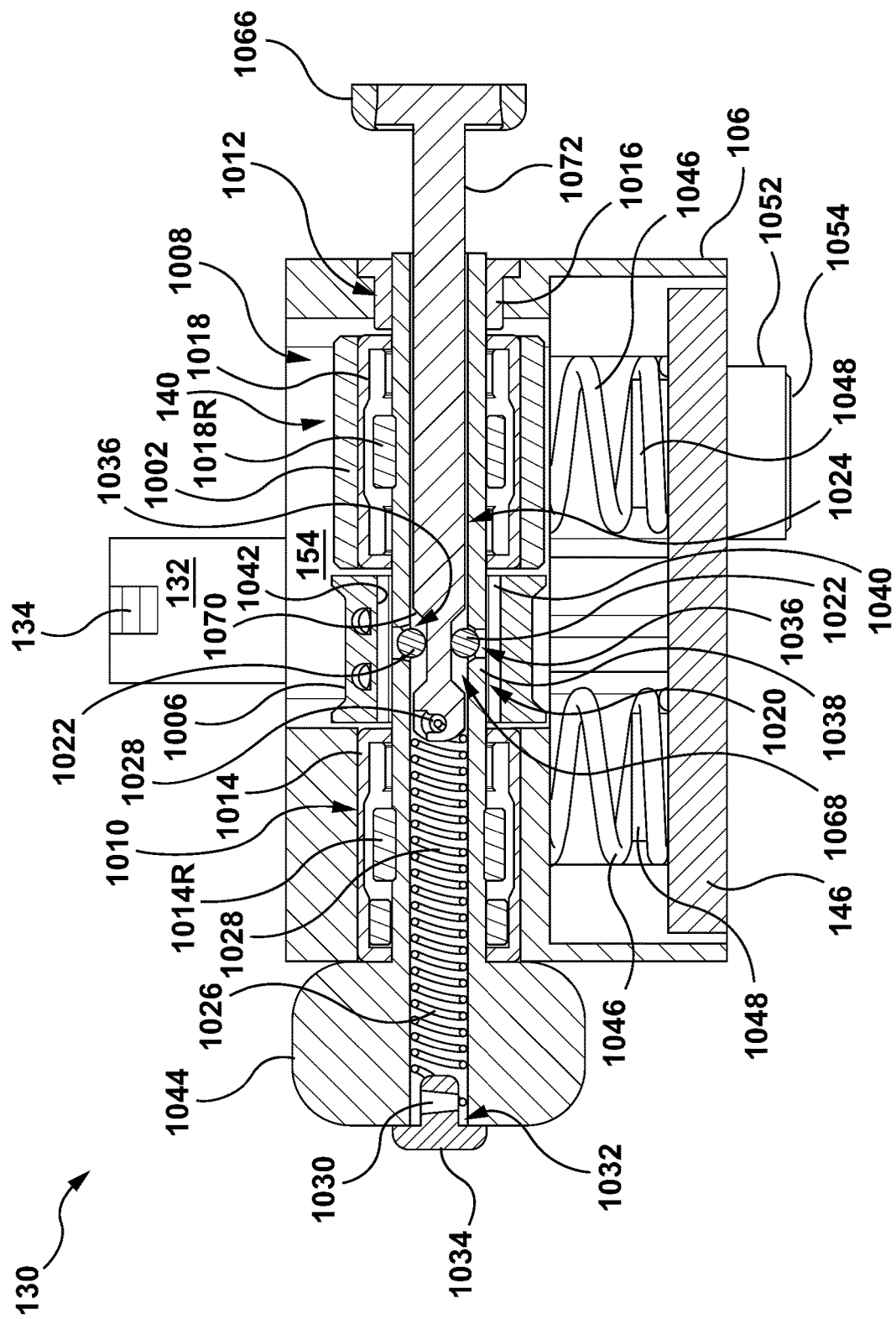

As noted above, in a preferred embodiment the locking mechanism is a releasable locking mechanism. Reference is now made to FIGS. 15A and 15B, which show an illustrative implementation of a releasable locking mechanism. In the illustrated embodiment, each spool 1006 is coupled to its respective main winch shaft 1020 by way of interengagement between the locking ball bearings 1022, the main winch shaft 1020, and the release shaft 1024 disposed concentrically within the lumen of the hollow main winch shaft 1020. Each release shaft 1024 is axially movable within its respective main winch shaft 1020, and is coupled to the main winch shaft 1020 by the release spring 1026 as described above, and the locking ball bearings 1022 are received within respective locating apertures 1036 extending through the annular wall 1038 of the respective main winch shaft 1020. When the release shaft 1024 is in a locking position relative to the main winch shaft 1020, as shown in FIG. 15A, the locking ball bearings 1022 are forced outwardly by the release shaft 1024 and engage with the locking channels 1040 in the inner surface 1042 of the respective spool 1006 so that rotation of the respective main winch shaft 1020 will result in rotation of the respective spool 1006. Conversely, the respective spool 1006 cannot rotate unless the respective main winch shaft 1020 also rotates, but such rotation in the unwinding direction of the respective spool 1006 is resisted by the respective winch needle bearing 1014 so that when the release shaft 1024 is in the locking position, tension on the respective cable 120 is maintained.

Reference is now made to FIG. 15B. In the illustrated embodiment, the release shaft 1024 can be moved axially relative to its respective main winch shaft 1020 by pulling on a release handle 1066 coupled to the ends of the release shafts 1024 opposite the ends having the eyes 1028. This extends the release spring 1026 which, when the force applied to the release handle 1066 is released, will return the release shaft 1024 to the locking position. Thus, in the illustrated embodiment the release shaft 1024 is biased into the locking position. By moving the release shaft 1024 axially relative to its respective main winch shaft 1020, the locking ball bearings 1022 can be disengaged from the locking channels 1040 in the inner surface 1042 of the respective spool 1006 so the respective spool 1006 can rotate freely in either direction relative to the respective main winch shaft 1020. This allows the respective spool 1006 to rotate relative to the respective main winch shaft 1020 in the unwinding direction to slacken the respective cable 120 and release tension therein. More particularly, in the illustrated embodiment, by moving the respective release shaft 1024 axially away from the manual tensioning knob 1044 of the respective main winch shaft 1020, an annular recess 1068 on the release shaft 1024 can be brought into registration with the locating apertures 1036 in the annular wall 1036 in the respective main winch shaft 1038. This is the release position of the release shaft 1024, relative to the respective main winch shaft 1038. When the annular recess 1068 on the release shaft 1024 is in registration with the locating apertures 1036 in the annular wall 1036 in the respective main winch shaft 1038, the locking ball bearings 1022 can move radially inwardly into the annular recess 1068, away from the inner surface 1042 of the spool 1006, while remaining trapped in the locating apertures 1036. This disengages the locking ball bearings 1022 from the locking channels 1040, allowing the respective spool 1006 to rotate freely relative to the respective main winch shaft 1038. The spring 1026 will return the release shaft 1024 to the locking position when the user lets go of the release handle 1066. As the release shaft 1024 moves axially back to the locking position (FIG. 15A), a beveled edge 1070 of the annular recess 1068 guides the locking ball bearings 1022 radially outwardly back onto the main body 1072 of the release shaft 1024. This moves the locking ball bearings 1022 radially outwardly through the locating apertures 1036 and back into engagement with the locking channels 1040 in the inner surface 1042 of the spool 1006. While the illustrative embodiment uses a single release handle 1066 for both release shafts 1024, other embodiments may provide for the release shafts to be manipulated individually.

As noted above, the panels 116 shown for the illustrative socket 100 are configured for a transtibial amputee. The same mechanism, including the winch assembly 130, movable platform 146 and resistive elements 1050, may also be used to apply tension to cables for tightening panels configured for a transfemoral amputee and thus the present disclosure encompasses a socket for a lower limb prosthesis for a transfemoral amputee.

The apparatus described above provides one illustrative, non-limiting implementation of a method for securing a residuum in a socket of a lower limb prosthesis. Motion from steps taken with the lower limb prosthesis is transmitted across a resilient resistive element to a reciprocal actuator to cycle the reciprocal actuator, with each cycle of the reciprocal actuator incrementally tightening a retention mechanism against the residuum, until a tightness threshold of the retention mechanism is reached. After the tightness threshold is reached, motion from further steps taken with the lower limb prosthesis is transmitted into the resistive element and the resistive element yields and absorbs the motion so that the reciprocal actuator fails to cycle on each further step, inhibiting further tightening of the retention mechanism beyond the threshold.

In the illustrative embodiment, the winch assembly 130 comprises two reciprocal actuators 140, which wind two cables 120 onto two spools 1006. It is contemplated that in other embodiments there may be a single reciprocal actuator, or more than two reciprocal actuator, and that there may be a single spool winding a single cable, or more than two spools winding more than two cables.

In the illustrative implementation described above, each cycle of the reciprocal actuator 140 incrementally winds a cable 120 around a spool 1006 to increase tension in the cable 120, which is coupled to the retention mechanism comprising the panels 116 such that increasing the tension in the cable 120 tightens the retention mechanism by forcing the panels 116 inwardly against the residuum, with a spring serving as the resistive element 1050. However, this is merely an illustrative, non-limiting mechanical implementation of the method, and other mechanical implementations are also contemplated.

One or more currently preferred embodiments have been described by way of example. It will be apparent to persons skilled in the art that a number of variations and modifications can be made without departing from the scope of the claims.

The following listing of reference characters is provided for convenience of reference only, and no limitation is implied:

100 Self-adjusting socket (generally)
102 Housing of self-adjusting socket
104 Receptacle body of housing
106 Actuator enclosure (winch body) of housing
108 Open end of receptacle body
110 Support end of receptacle body
112 Residuum receptacle
114 Mounting block
116 Panels
118 Openings in receptacle body
120 Cables
122 Cable tunnels in panels
124 Cable guides on receptacle body
126 Port
128 Passageway through support end of receptacle body
130 Winch assembly
132 Locking post
134 Locking lugs
136 Locking aperture
138 Locking recesses
140 Reciprocal actuators
146 Movable platform
148 Dovetail guide follower
150 Guide channel
152 Elongate inward projection
154 Interior sidewall
1002 Actuator body
1004 Actuator arm
1006 Spool
1008 Winch cavities
1010 Bushing aperture
1012 Bearing aperture
1014 Winch needle bearing
1014R Winch needle bearing rollers
1016 Winch bushing
1018R Actuator needle bearing
1018 Actuator needle bearing rollers
1020 Main winch shaft
1022 Locking ball bearings
1024 Release shaft
1026 Release spring
1028 Eye of release shaft
1030 Eye of spring retainer
1032 Spring retainer
1034 End cap of spring retainer
1036 Locating apertures
1038 Annular wall of main winch shaft
1040 Locking channels
1042 Inner surface of spool
1044 Manual tensioning knob
1046 Cushioning springs
1048 Locating studs
1050 Resistive elements
1052 Cylinder barrel
1054 Setscrew
1056 Piston
1058 Head of cylinder
1060 Piston rod
1062 Rod aperture
1063 T-shaped slot in actuator arm
1064 Piston rod connector
1066 Release handle
1068 Annular recess in release shaft
1070 Beveled edge of annular recess
1072 Main body of release shaft

What is claimed is:

1. A self-adjusting socket for a lower limb prosthesis, comprising:
a housing comprising a residuum receptacle;
a retention mechanism carried by the housing and configured for retaining a residuum within the residuum receptacle;
at least one actuator carried by the housing and coupled to the retention mechanism through a respective mechanical linkage, the at least one actuator configured to reciprocally cycle between a rest position and an actuated position and to act through the respective mechanical linkage to incrementally further tighten the retention mechanism against the residuum on each movement of the at least one actuator into the actuated position and leave the retention mechanism further incrementally tightened upon each return of the actuator to the rest position;
a releasable locking mechanism carried by the housing and configured to maintain tightness of the retention mechanism against the residuum after each cycle of the at least one actuator;
the housing configured so that each step transmits motion to a respective resilient resistive element coupled to a respective one of the at least one actuator, wherein:
when a tightness of the retention mechanism is below a threshold, each step transmits motion across the respective resistive element to the respective actuator to cycle the respective actuator to further tighten the retention mechanism; and
when the tightness of the retention mechanism has reached the threshold, on each further step the respective resistive element yields to absorb the motion, so that the respective actuator fails to cycle on each further step, inhibiting further tightening of the retention mechanism beyond the threshold;
further comprising a manual tightening mechanism for tightening the retention mechanism.

2. The socket of claim 1, wherein the manual tightening mechanism comprises a knob.

3. The socket of claim 1, wherein the at least one resistive element is at least one spring.

4. A self-adjusting socket for a lower limb prosthesis, comprising:
a housing comprising a residuum receptacle;

a retention mechanism carried by the housing and configured for retaining a residuum within the residuum receptacle;

at least one actuator carried by the housing and coupled to the retention mechanism through a respective mechanical linkage, the at least one actuator configured to reciprocally cycle between a rest position and an actuated position and to act through the respective mechanical linkage to incrementally further tighten the retention mechanism against the residuum on each movement of the at least one actuator into the actuated position and leave the retention mechanism further incrementally tightened upon each return of the actuator to the rest position;

a releasable locking mechanism carried by the housing and configured to maintain tightness of the retention mechanism against the residuum after each cycle of the at least one actuator;

the housing configured so that each step transmits motion to a respective resilient resistive element coupled to a respective one of the at least one actuator, wherein:

when a tightness of the retention mechanism is below a threshold, each step transmits motion across the respective resistive element to the respective actuator to cycle the respective actuator to further tighten the retention mechanism; and when the tightness of the retention mechanism has reached the threshold, on each further step the respective resistive element yields to absorb the motion, so that the respective actuator fails to cycle on each further step, inhibiting further tightening of the retention mechanism beyond the threshold;

wherein:

the retention mechanism comprises at least one panel movably carried by the housing; the at least one panel being movable inwardly and outwardly relative to the residuum receptacle; and the at least one actuator is configured to act through the respective mechanical linkage to incrementally move the at least one panel inwardly to tighten the at least one panel against the residuum on each cycle of the at least one actuator.

5. The socket of claim 4, wherein the at least one panel comprises a plurality of panels arranged circumferentially about the residuum receptacle.

6. The socket of claim 5, where the panels are disposed in respective openings so as to be inwardly and outwardly displaceable relative to the housing.

7. The socket of claim 6, wherein:

the mechanical linkage comprises at least one cable coupled to at least one of the panels;

each respective actuator is configured to incrementally increase tension in a respective one of the at least one cable on each cycle of the respective actuator; and incrementally increasing the tension on the respective cable moves the respective panels inwardly relative to the residuum receptacle.

8. The socket of claim 7, wherein:

the housing carries a movable platform;

the platform is reciprocally movable toward and away from the residuum receptacle between a distal position and a proximal position;

the platform is biased into the distal position;

the at least one actuator is carried by the housing between the residuum receptacle and the platform;

the respective resistive element is trapped between the platform and the respective actuator whereby movement of the platform toward the proximal position pushes the resistive element toward the respective actuator;

wherein reciprocal movement of the platform into the proximal position and back to the distal position cycles the respective actuator only where a resistance to compression of the respective resistive element exceeds a resistance to movement from the tension in the respective cable so that the respective resistive element transmits the movement of the platform to the respective actuator instead of yielding to the movement of the platform.

9. The socket of claim 8, wherein:

each actuator comprises a rocker coupled to a respective spool; and each cycle of the rocker indexes the spool to wind the respective cable onto the spool to incrementally increase the tension in the respective cable.

10. The socket of claim 9, wherein:

each rocker comprises a respective outwardly extending actuator arm that acts as a lever to pivot the rocker; and where the resistance to compression of the respective resistive element exceeds a resistance to movement from the tension in the cable, the resistive element transmits the movement of the platform into the proximal position to the actuator arm to pivot the rocker and thereby index the spool.

11. The socket of claim 10, wherein the at least one resistive element is at least one spring.

12. A method for securing a residuum in a socket of a lower limb prosthesis, the method comprising:

Providing the socket comprising:

A housing comprising a residuum receptacle;

A retention mechanism carried by the housing and configured for retaining the residuum within the residuum receptacle;

at least one actuator carried by the housing and coupled to the retention mechanism through a respective mechanical linkage, the at least one actuator configured to reciprocally cycle between a rest position and an actuated position and to act through the respective mechanical linkage to incrementally further tighten the retention mechanism against the residuum on each movement of the late last one actuator into the actuated position and leave the retention mechanism further incrementally tightened upon each return of the actuator into a rest position;

a releasable locking mechanism carried by the housing and configured to maintain tightness of the retention mechanism against the residuum after each cycle of the at least one actuator further comprising a manual tightening mechanism for tightening the retention mechanism;

Performing the steps of:

transmitting motion from steps taken with the lower limb prosthesis across a resilient resistive element to the actuator to cycle the actuator, wherein each cycle of the actuator incrementally tightens the retention mechanism against the residuum, until a tightness threshold of the retention mechanism is reached;

and after the tightness threshold is reached, transmitting motion from further steps taken with the lower limb prosthesis into the resistive element wherein the resistive element yields and absorbs the motion so that the actuator fails to cycle on each further step, inhibiting further tightening of the retention mechanism beyond the threshold.

13. The method of claim 12, wherein:
each cycle of the actuator incrementally winds a cable around a spool to increase tension in the cable;
the cable is coupled to the retention mechanism and increasing the tension in the cable tightens the retention mechanism.

14. The method of claim 13, wherein increasing the tension in the cable tightens the retention mechanism by forcing a panel inwardly against the residuum.

15. The method of claim 12, wherein the resistive element is a spring.

16. A method for tightening a panel in a receptacle for a residuum, the method comprising:
Providing a self-adjusting socket comprising:
A housing comprising the residuum receptacle;
A retention mechanism carried by the housing and configured for retaining the residuum within the residuum receptacle;
at least one actuator carried by the housing and coupled to the retention mechanism through a respective mechanical linkage, the at least one actuator configured to reciprocally cycle between a rest position and an actuated position and to act through the respective mechanical linkage to incrementally further tighten the retention mechanism against the residuum on each movement of the late last one actuator into the actuated position and leave the retention mechanism further incrementally tightened upon each return of the actuator into a rest position;
a releasable locking mechanism carried by the housing and configured to maintain tightness of the retention mechanism against the residuum after each cycle of the at least one actuator further comprising a manual tightening mechanism for tightening the retention mechanism;
the housing configured so that each step transmits motion to a respective resilient resistive element coupled to a respective one of the at least one actuator, wherein when a tightness of the retention mechanism is below a threshold, each step transmits motion across the respective resistive element to the respective actuator to cycle the respective actuator to further tighten the retention mechanism;
and when the tightness of the retention mechanism has reached the threshold, on each further step the respective resistive element yields to absorb the motion, so that the respective actuator fails to cycle on each further step, inhibiting further tightening of the retention mechanism beyond the threshold;
further comprising a manual tightening mechanism for tightening the retention mechanism;
Performing the steps of:
applying incremental tension across the panel to move the panel inwardly relative to the receptacle, wherein:
the incremental tension is applied by transmission of movement of an end effector of a lower limb prosthesis toward the residuum through a mechanical interface to a tensioner;
and the movement is transmitted to the tensioner only when a resistance of the mechanical interface exceeds a current tension applied by the tensioner.

17. The method of claim 16, wherein the resistance of the mechanical interface is provided by at least one spring.

18. The method of claim 16, wherein the tensioner comprises a winch.

* * * * *